US009629626B2

(12) United States Patent
Soltz et al.

(10) Patent No.: US 9,629,626 B2
(45) Date of Patent: Apr. 25, 2017

(54) MECHANICALLY TUNED BUTTRESS MATERIAL TO ASSIST WITH PROPER FORMATION OF SURGICAL ELEMENT IN DISEASED TISSUE

(75) Inventors: Michael A. Soltz, North Haven, CT (US); Megan L. Prommersberger, Wallingford, CT (US); Joshua Stopek, Yalesville, CT (US)

(73) Assignee: Covidien LP, Mansfield, MA (US)

( * ) Notice: Subject to any disclaimer, the term of this patent is extended or adjusted under 35 U.S.C. 154(b) by 2190 days.

(21) Appl. No.: 11/408,492

(22) Filed: Apr. 21, 2006

(65) Prior Publication Data

US 2007/0179528 A1    Aug. 2, 2007

Related U.S. Application Data

(60) Provisional application No. 60/764,451, filed on Feb. 2, 2006, provisional application No. 60/764,449, filed on Feb. 2, 2006.

(51) Int. Cl.
*A61B 17/072* (2006.01)
*A61B 17/115* (2006.01)
*A61B 90/00* (2016.01)

(52) U.S. Cl.
CPC ...... *A61B 17/072* (2013.01); *A61B 17/07207* (2013.01); *A61B 17/07292* (2013.01); *A61B 17/115* (2013.01); *A61B 2090/064* (2016.02); *A61B 2090/0807* (2016.02)

(58) Field of Classification Search
CPC ............ A61B 17/072; A61B 17/07207; A61B 17/07292; A61B 17/115; A61B 17/1152; A61B 17/1155; A61B 17/1157; A61B 2090/064; A61B 2090/065; A61B 2017/1157

USPC ........ 600/587, 553, 561; 606/139, 140, 142, 606/143, 144, 148, 149, 150, 151
See application file for complete search history.

(56) References Cited

U.S. PATENT DOCUMENTS

| | | | |
|---|---|---|---|
| 3,054,406 A | | 9/1962 | Usher |
| 3,124,136 A | | 3/1964 | Usher |
| 3,469,439 A | * | 9/1969 | Roberts et al. ................ 73/762 |
| 3,748,758 A | | 7/1973 | Wilchusky |

(Continued)

FOREIGN PATENT DOCUMENTS

| | | |
|---|---|---|
| DE | 1 99 24 311 A1 | 11/2000 |
| DE | 199 24 311 A1 | 11/2000 |

(Continued)

OTHER PUBLICATIONS

Japanese to English Machine translation of JP 2002202213 A from the Japanese Patent Office Website. Sep. 18, 2013.*

(Continued)

*Primary Examiner* — Adam J Eiseman

(57) ABSTRACT

An apparatus for supporting tissue during compression prior to the insertion of a surgical element into the tissue has a substrate. The substrate is made from a predetermined material. The predetermined material has a thickness and a predetermined stress strain profile. The predetermined stress strain profile is complementary to a stress strain profile of the tissue and permits the substrate to support the tissue when the surgical element is delivered into the tissue. The substrate provides hemostasis control of the tissue when the surgical element is delivered into the tissue.

19 Claims, 11 Drawing Sheets

(56) References Cited

U.S. PATENT DOCUMENTS

| | | | |
|---|---|---|---|
| 4,347,847 | A | 9/1982 | Usher |
| 4,354,628 | A | 10/1982 | Green |
| 4,452,245 | A | 6/1984 | Usher |
| 4,473,077 | A | 9/1984 | Noiles et al. |
| 4,576,167 | A | 3/1986 | Noiles |
| 4,605,730 | A | 8/1986 | Shalaby et al. |
| 4,646,745 | A | 3/1987 | Noiles |
| 4,655,221 | A | 4/1987 | Devereux |
| 4,834,090 | A | 5/1989 | Moore |
| 4,838,884 | A | 6/1989 | Dumican et al. |
| 4,927,640 | A | 5/1990 | Dahlinder et al. |
| 4,930,674 | A | 6/1990 | Barak |
| 5,002,551 | A | 3/1991 | Linsky et al. |
| 5,005,749 | A | 4/1991 | Aranyi |
| 5,014,899 | A | 5/1991 | Presty et al. |
| 5,040,715 | A | 8/1991 | Green et al. |
| 5,065,929 | A | 11/1991 | Schulze et al. |
| 5,119,983 | A | 6/1992 | Green et al. |
| 5,205,459 | A | 4/1993 | Brinkerhoff et al. |
| 5,263,629 | A | 11/1993 | Trumbull et al. |
| 5,307,976 | A | 5/1994 | Olson et al. |
| 5,312,023 | A | 5/1994 | Green et al. |
| 5,314,471 | A | 5/1994 | Brauker et al. |
| 5,318,221 | A | 6/1994 | Green et al. |
| 5,326,013 | A | 7/1994 | Green et al. |
| 5,332,142 | A | 7/1994 | Robinson et al. |
| 5,344,454 | A | 9/1994 | Clarke et al. |
| 5,389,098 | A * | 2/1995 | Tsuruta et al. .................. 606/41 |
| 5,392,979 | A | 2/1995 | Green et al. |
| 5,395,033 | A | 3/1995 | Byrne et al. |
| 5,397,324 | A | 3/1995 | Carroll et al. |
| 5,425,745 | A | 6/1995 | Green et al. |
| 5,441,193 | A | 8/1995 | Gravener |
| 5,441,507 | A | 8/1995 | Wilk et al. |
| 5,443,198 | A | 8/1995 | Viola et al. |
| 5,468,253 | A | 11/1995 | Bezwada et al. |
| 5,474,967 | A * | 12/1995 | Komatsu et al. ............. 503/215 |
| 5,503,638 | A | 4/1996 | Cooper et al. |
| 5,542,594 | A | 8/1996 | McKean et al. |
| 5,549,628 | A | 8/1996 | Cooper et al. |
| 5,575,803 | A | 11/1996 | Cooper et al. |
| 5,588,579 | A | 12/1996 | Schnut et al. |
| 5,653,756 | A | 8/1997 | Clarke et al. |
| 5,683,809 | A | 11/1997 | Freeman et al. |
| 5,690,675 | A | 11/1997 | Sawyer et al. |
| 5,702,409 | A | 12/1997 | Rayburn et al. |
| 5,752,965 | A | 5/1998 | Francis et al. |
| 5,762,256 | A | 6/1998 | Mastri et al. |
| 5,766,188 | A | 6/1998 | Igaki |
| 5,769,892 | A | 6/1998 | Kingwell |
| 5,782,396 | A | 7/1998 | Mastri et al. |
| 5,799,857 | A | 9/1998 | Robertson et al. |
| 5,810,855 | A | 9/1998 | Rayburn et al. |
| 5,814,057 | A | 9/1998 | Oi et al. |
| 5,833,695 | A | 11/1998 | Yoon |
| 5,843,096 | A | 12/1998 | Igaki et al. |
| 5,895,412 | A | 4/1999 | Tucker |
| 5,902,312 | A | 5/1999 | Frater et al. |
| 5,908,427 | A | 6/1999 | McKean et al. |
| 5,915,616 | A | 6/1999 | Viola et al. |
| 5,931,847 | A | 8/1999 | Bittner et al. |
| 5,964,774 | A | 10/1999 | McKean et al. |
| 5,997,895 | A | 12/1999 | Narotam et al. |
| 6,019,791 | A | 2/2000 | Wood |
| 6,030,392 | A | 2/2000 | Dakov et al. |
| 6,032,849 | A | 3/2000 | Mastri et al. |
| 6,045,560 | A | 4/2000 | McKean et al. |
| 6,053,390 | A | 4/2000 | Green et al. |
| 6,063,097 | A | 5/2000 | Oi et al. |
| 6,080,169 | A | 6/2000 | Turtel |
| 6,099,551 | A | 8/2000 | Gabbay |
| 6,149,667 | A | 11/2000 | Hovland et al. |
| 6,155,265 | A | 12/2000 | Hammerslag |
| 6,210,439 | B1 | 4/2001 | Firmin et al. |
| 6,214,020 | B1 | 4/2001 | Mulhauser et al. |
| 6,241,139 | B1 | 6/2001 | Milliman et al. |
| 6,258,107 | B1 | 7/2001 | Balazs et al. |
| 6,267,772 | B1 | 7/2001 | Mulhauser et al. |
| 6,273,897 | B1 | 8/2001 | Dalessandro et al. |
| 6,280,453 | B1 | 8/2001 | Kugel et al. |
| 6,299,631 | B1 | 10/2001 | Shalaby |
| 6,312,457 | B1 | 11/2001 | DiMatteo et al. |
| 6,312,474 | B1 | 11/2001 | Francis et al. |
| 6,325,810 | B1 | 12/2001 | Hamilton et al. |
| 6,436,030 | B2 | 8/2002 | Rehil |
| 6,454,780 | B1 | 9/2002 | Wallace |
| 6,461,368 | B2 | 10/2002 | Fogarty et al. |
| 6,503,257 | B2 | 1/2003 | Grant et al. |
| 6,514,283 | B2 | 2/2003 | DiMatteo et al. |
| 6,517,566 | B1 | 2/2003 | Hovland et al. |
| 6,551,356 | B2 | 4/2003 | Rousseau |
| 6,592,597 | B2 | 7/2003 | Grant et al. |
| 6,638,285 | B2 | 10/2003 | Gabbay |
| 6,652,594 | B2 | 11/2003 | Francis et al. |
| 6,656,193 | B2 | 12/2003 | Grant |
| 6,669,735 | B1 | 12/2003 | Pelissier |
| 6,677,258 | B2 | 1/2004 | Carroll et al. |
| 6,685,714 | B2 | 2/2004 | Rousseau |
| 6,704,210 | B1 | 3/2004 | Myers |
| 6,723,114 | B2 | 4/2004 | Shalaby |
| 6,726,706 | B2 | 4/2004 | Dominguez |
| 6,736,823 | B2 | 5/2004 | Darois et al. |
| 6,736,854 | B2 | 5/2004 | Vadurro et al. |
| 6,746,458 | B1 | 6/2004 | Cloud |
| 6,773,458 | B2 | 8/2004 | Brauker et al. |
| 6,927,315 | B1 | 8/2005 | Heinecke et al. |
| 6,959,851 | B2 | 11/2005 | Heinrich |
| 7,128,748 | B2 | 10/2006 | Mooradian et al. |
| 7,147,138 | B2 | 12/2006 | Shelton, IV |
| 7,434,717 | B2 | 10/2008 | Shelton, IV et al. |
| 7,438,209 | B1 | 10/2008 | Hess et al. |
| 7,547,312 | B2 | 6/2009 | Bauman et al. |
| 7,559,937 | B2 | 7/2009 | de la Torre et al. |
| 7,604,151 | B2 | 10/2009 | Hess et al. |
| 7,665,646 | B2 | 2/2010 | Prommersberger |
| 7,669,747 | B2 | 3/2010 | Weisenburgh, II et al. |
| 7,717,313 | B2 | 5/2010 | Bettuchi et al. |
| 7,722,642 | B2 | 5/2010 | Williamson, IV |
| 7,744,627 | B2 | 6/2010 | Orban, III et al. |
| 7,776,060 | B2 | 8/2010 | Mooradian |
| 7,793,813 | B2 | 9/2010 | Bettuchi |
| 7,799,026 | B2 | 9/2010 | Schechter et al. |
| 7,823,592 | B2 | 11/2010 | Bettuchi et al. |
| 7,845,533 | B2 | 12/2010 | Marczyk et al. |
| 7,845,536 | B2 | 12/2010 | Viola et al. |
| 7,846,149 | B2 | 12/2010 | Jankowski |
| 7,909,224 | B2 | 3/2011 | Prommersberger |
| 7,950,561 | B2 | 5/2011 | Aranyi |
| 7,951,166 | B2 | 5/2011 | Orban |
| 7,967,179 | B2 | 6/2011 | Olson |
| 7,988,027 | B2 | 8/2011 | Olson |
| 8,011,550 | B2 | 9/2011 | Aranyi |
| 8,016,177 | B2 | 9/2011 | Bettuchi |
| 8,016,178 | B2 | 9/2011 | Olson |
| 8,028,883 | B2 | 10/2011 | Stopek |
| 8,062,330 | B2 | 11/2011 | Prommersberger |
| 8,083,119 | B2 | 12/2011 | Prommersberger |
| 8,123,766 | B2 | 2/2012 | Bauman |
| 8,123,767 | B2 | 2/2012 | Bauman |
| 8,146,791 | B2 | 4/2012 | Bettuchi |
| 8,157,149 | B2 | 4/2012 | Olson |
| 8,157,151 | B2 | 4/2012 | Ingmanson |
| 8,167,895 | B2 | 5/2012 | D'Agostino |
| 8,192,460 | B2 | 6/2012 | Orban |
| 8,210,414 | B2 | 7/2012 | Bettuchi |
| 8,225,799 | B2 | 7/2012 | Bettuchi |
| 8,225,981 | B2 | 7/2012 | Criscuolo et al. |
| 8,231,043 | B2 | 7/2012 | Tarinelli |
| 8,235,273 | B2 | 8/2012 | Olson |
| 8,245,901 | B2 | 8/2012 | Stopek |
| 8,256,654 | B2 | 9/2012 | Bettuchi |
| 8,257,391 | B2 | 9/2012 | Orban |
| 8,276,800 | B2 | 10/2012 | Bettuchi |
| 8,286,849 | B2 | 10/2012 | Bettuchi |

(56) References Cited

U.S. PATENT DOCUMENTS

| | | |
|---|---|---|
| 8,308,042 B2 | 11/2012 | Aranyi |
| 8,308,045 B2 | 11/2012 | Bettuchi |
| 8,308,046 B2 | 11/2012 | Prommersberger |
| 8,312,885 B2 | 11/2012 | Bettuchi |
| 8,313,014 B2 | 11/2012 | Bettuchi |
| 8,348,126 B2 | 1/2013 | Olson |
| 8,348,130 B2 | 1/2013 | Shah |
| 8,365,972 B2 | 2/2013 | Aranyi et al. |
| 8,371,491 B2 | 2/2013 | Huitema |
| 8,371,492 B2 | 2/2013 | Aranyi |
| 8,371,493 B2 | 2/2013 | Aranyi |
| 8,393,514 B2 | 3/2013 | Shelton, IV |
| 8,408,440 B2 | 4/2013 | Olson |
| 8,413,871 B2 | 4/2013 | Racenet |
| 8,424,742 B2 | 4/2013 | Bettuchi |
| 8,453,652 B2 | 6/2013 | Stopek |
| 8,453,904 B2 | 6/2013 | Eskaros |
| 8,453,909 B2 | 6/2013 | Olson |
| 8,453,910 B2 | 6/2013 | Bettuchi |
| 8,464,925 B2 | 6/2013 | Hull et al. |
| 8,474,677 B2 | 7/2013 | Woodard, Jr. |
| 8,479,968 B2 | 7/2013 | Hodgkinson |
| 8,485,414 B2 | 7/2013 | Criscuolo et al. |
| 8,496,683 B2 | 7/2013 | Prommersberger |
| 8,511,533 B2 | 8/2013 | Viola |
| 8,512,402 B2 | 8/2013 | Marczyk |
| 8,529,600 B2 | 9/2013 | Woodard, Jr. |
| 8,540,131 B2 | 9/2013 | Swayze |
| 8,551,138 B2 | 10/2013 | Orban |
| 8,556,918 B2 | 10/2013 | Bauman |
| 8,561,873 B2 | 10/2013 | Ingmanson |
| 8,584,920 B2 | 11/2013 | Hodgkinson |
| 8,590,762 B2 | 11/2013 | Hess |
| 8,616,430 B2 | 12/2013 | Prommersberger |
| 8,631,989 B2 | 1/2014 | Aranyi |
| 8,668,129 B2 | 3/2014 | Olson |
| 8,684,250 B2 | 4/2014 | Bettuchi |
| 2002/0016626 A1 | 2/2002 | DiMatteo et al. |
| 2002/0019187 A1 | 2/2002 | Carroll et al. |
| 2002/0028243 A1 | 3/2002 | Masters |
| 2002/0052622 A1 | 5/2002 | Rousseau |
| 2002/0091397 A1 | 7/2002 | Chen |
| 2002/0133236 A1 | 9/2002 | Rousseau |
| 2002/0138152 A1 | 9/2002 | Francis et al. |
| 2002/0151911 A1 | 10/2002 | Gabbay |
| 2002/0165559 A1 | 11/2002 | Grant et al. |
| 2002/0165562 A1 | 11/2002 | Grant et al. |
| 2002/0165563 A1 | 11/2002 | Grant et al. |
| 2002/0177859 A1 | 11/2002 | Monassevitch et al. |
| 2003/0059463 A1* | 3/2003 | Lahtinen ............... 424/450 |
| 2003/0065345 A1 | 4/2003 | Weadock |
| 2003/0065346 A1 | 4/2003 | Evens et al. |
| 2003/0083676 A1 | 5/2003 | Wallace |
| 2003/0088256 A1 | 5/2003 | Conston et al. |
| 2003/0105510 A1 | 6/2003 | DiMatteo et al. |
| 2003/0114866 A1 | 6/2003 | Ulmsten et al. |
| 2003/0120284 A1 | 6/2003 | Palacios |
| 2003/0167064 A1 | 9/2003 | Whayne |
| 2003/0181927 A1 | 9/2003 | Wallace |
| 2003/0183671 A1 | 10/2003 | Mooradian et al. |
| 2003/0208231 A1 | 11/2003 | Williamson, IV et al. |
| 2004/0034377 A1 | 2/2004 | Sharkawy et al. |
| 2004/0092960 A1 | 5/2004 | Abrams et al. |
| 2004/0093029 A1 | 5/2004 | Zubik et al. |
| 2004/0107006 A1 | 6/2004 | Francis et al. |
| 2004/0116945 A1 | 6/2004 | Sharkawy et al. |
| 2004/0142621 A1 | 7/2004 | Carroll et al. |
| 2004/0143263 A1 | 7/2004 | Schechter et al. |
| 2004/0172048 A1 | 9/2004 | Browning |
| 2004/0209059 A1 | 10/2004 | Foss |
| 2004/0215214 A1 | 10/2004 | Crews et al. |
| 2004/0215219 A1 | 10/2004 | Eldridge et al. |
| 2004/0215221 A1 | 10/2004 | Suyker et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021026 A1 | 1/2005 | Baily |
| 2005/0021053 A1 | 1/2005 | Heinrich |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0143756 A1 | 6/2005 | Jankowski |
| 2005/0149073 A1 | 7/2005 | Arani et al. |
| 2005/0228446 A1 | 10/2005 | Mooradian et al. |
| 2005/0245965 A1 | 11/2005 | Orban et al. |
| 2006/0004407 A1 | 1/2006 | Hiles et al. |
| 2006/0085034 A1 | 4/2006 | Bettuchi |
| 2006/0135992 A1 | 6/2006 | Bettuchi |
| 2006/0173470 A1 | 8/2006 | Oray et al. |
| 2006/0178683 A1 | 8/2006 | Shimoji et al. |
| 2006/0212050 A1 | 9/2006 | D'Agostino et al. |
| 2006/0212069 A1* | 9/2006 | Shelton ............... 606/205 |
| 2006/0271104 A1 | 11/2006 | Viola et al. |
| 2006/0273135 A1* | 12/2006 | Beetel ............... 227/175.1 |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0246505 A1 | 10/2007 | Pace-Floridia et al. |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0200949 A1 | 8/2008 | Hiles |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0065606 A1 | 3/2010 | Stopek |
| 2010/0065607 A1 | 3/2010 | Orban, III et al. |
| 2010/0072254 A1 | 3/2010 | Aranyi et al. |
| 2010/0147921 A1 | 6/2010 | Olson |

(56) References Cited

U.S. PATENT DOCUMENTS

| | | |
|---|---|---|
| 2010/0147922 A1 | 6/2010 | Olson |
| 2010/0147923 A1 | 6/2010 | D'Agostino et al. |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0087279 A1 | 4/2011 | Shah et al. |
| 2012/0187179 A1 | 7/2012 | Gleiman |
| 2012/0273547 A1 | 11/2012 | Hodgkinson et al. |
| 2013/0037596 A1 | 2/2013 | Bear et al. |
| 2013/0105548 A1 | 5/2013 | Hodgkinson |
| 2013/0105553 A1 | 5/2013 | Racenet |
| 2013/0112732 A1 | 5/2013 | Aranyi |
| 2013/0112733 A1 | 5/2013 | Aranyi |
| 2013/0153633 A1 | 6/2013 | Casasanta |
| 2013/0153634 A1 | 6/2013 | Carter |
| 2013/0153635 A1 | 6/2013 | Hodgkinson |
| 2013/0153638 A1 | 6/2013 | Carter |
| 2013/0153639 A1 | 6/2013 | Hodgkinson |
| 2013/0153640 A1 | 6/2013 | Hodgkinson |
| 2013/0181031 A1 | 7/2013 | Olson |
| 2013/0193186 A1 | 8/2013 | Racenet |
| 2013/0193190 A1 | 8/2013 | Carter |
| 2013/0193191 A1 | 8/2013 | Stevenson |
| 2013/0193192 A1 | 8/2013 | Casasanta |
| 2013/0209659 A1 | 8/2013 | Racenet |
| 2013/0221062 A1 | 8/2013 | Hodgkinson |
| 2013/0240600 A1 | 9/2013 | Bettuchi |
| 2013/0240601 A1 | 9/2013 | Bettuchi |
| 2013/0240602 A1 | 9/2013 | Stopek |
| 2013/0277411 A1 | 10/2013 | Hodgkinson |
| 2013/0306707 A1 | 11/2013 | Viola |
| 2013/0310873 A1 | 11/2013 | Prommersberger |
| 2013/0327807 A1 | 12/2013 | Olson |
| 2014/0012317 A1 | 1/2014 | Orban |
| 2014/0021242 A1 | 1/2014 | Hodgkinson |
| 2014/0027490 A1 | 1/2014 | Marczyk |
| 2014/0034704 A1 | 2/2014 | Ingmanson |
| 2014/0048580 A1 | 2/2014 | Merchant |
| 2014/0061280 A1 | 3/2014 | Ingmanson |
| 2014/0061281 A1 | 3/2014 | Hodgkinson |

FOREIGN PATENT DOCUMENTS

| | | |
|---|---|---|
| EP | 0 594 148 A1 | 4/1994 |
| EP | 0 327 022 B1 | 4/1995 |
| EP | 0 667 119 A1 | 8/1995 |
| EP | 1 064 883 A1 | 1/2001 |
| EP | 1 064883 A1 | 1/2001 |
| EP | 1 256 317 A2 | 11/2002 |
| EP | 1 520 525 A1 | 4/2005 |
| EP | 1 621 141 A2 | 2/2006 |
| EP | 1 702 570 A1 | 9/2006 |
| EP | 1 759 640 A2 | 3/2007 |
| EP | 1 815 804 A2 | 8/2007 |
| EP | 1 825 820 | 8/2007 |
| EP | 1 929 958 | 6/2008 |
| EP | 1 994 890 A1 | 11/2008 |
| EP | 2 005 894 A2 | 12/2008 |
| EP | 2 005 895 A2 | 12/2008 |
| EP | 2 008 595 A2 | 12/2008 |
| EP | 2 090 231 | 8/2009 |
| EP | 2 090 244 | 8/2009 |
| EP | 2 090 252 | 8/2009 |
| EP | 2 198 787 A1 | 6/2010 |
| EP | 2 236 098 A2 | 10/2010 |
| EP | 2 311 386 | 4/2011 |
| EP | 2 462 880 | 6/2012 |
| EP | 2 517 637 | 10/2012 |
| EP | 2 620 106 | 7/2013 |
| EP | 2 630 922 | 8/2013 |
| EP | 2 644 125 | 10/2013 |
| JP | 09 054043 A | 2/1997 |
| JP | 2000-166933 | 6/2000 |
| JP | 2002-202213 | 7/2002 |
| JP | 2002 202213 A | 7/2002 |
| JP | 2002202213 A * | 7/2002 |
| JP | 2006 028202 A | 2/2006 |
| JP | 07-124166 | 5/2007 |
| WO | WO 90/05489 A1 | 5/1990 |
| WO | WO 95/16221 | 6/1995 |
| WO | WO 95/16221 A | 6/1995 |
| WO | WO 96/22055 A1 | 7/1996 |
| WO | WO 97/01989 A1 | 1/1997 |
| WO | WO 97/13463 A1 | 4/1997 |
| WO | WO 98/17180 A1 | 4/1998 |
| WO | WO 99/45849 A1 | 9/1999 |
| WO | WO 03/082126 A1 | 10/2003 |
| WO | WO 03/088845 | 10/2003 |
| WO | WO 03/094743 | 11/2003 |
| WO | WO 03/105698 A2 | 12/2003 |
| WO | WO 2005/079675 | 9/2005 |
| WO | WO 2006/023578 A2 | 3/2006 |
| WO | WO 2006/044490 A2 | 4/2006 |
| WO | WO 2006/083748 A1 | 8/2006 |
| WO | WO 2007/121579 A1 | 11/2007 |
| WO | WO 2008/057281 A2 | 5/2008 |
| WO | WO 2008/109125 A1 | 9/2008 |
| WO | WO 2010/075298 A2 | 7/2010 |
| WO | WO 2011/143183 A2 | 11/2011 |
| WO | WO 2012/044848 A1 | 4/2012 |

OTHER PUBLICATIONS

European Search Report for corresponding European Patent Application—EP07002328—Date of Mailing Sep. 27, 2007 (4 pages).

International Search Report corresponding to European Application No. EP 12 15 2229.6, completed on Feb. 23, 2012 and mailed on Mar. 1, 2012; 4 pages.

International Search Report corresponding to European Application No. EP 12 15 0511.9, completed on Apr. 16, 2012 and mailed on Apr. 24, 2012; 7 pages.

International Search Report corresponding to European Application No. EP 12 15 2541.4, completed on Apr. 23, 2012 and mailed on May 3, 2012; 10 pages.

International Search Report corresponding to European Application No. EP 12 16 5609.4, completed on Jul. 5, 2012 and mailed on Jul. 13, 2012; 8 pages.

International Search Report corresponding to European Application No. EP 12 15 8861.0, completed on Jul. 17, 2012 and mailed on Jul. 24, 2012; 9 pages.

International Search Report corresponding to European Application No. EP 12 16 5878.5, completed on Jul. 24, 2012 and mailed on Aug. 6, 2012; 8 pages.

International Search Report corresponding to European Application No. EP 11 18 8309.6, completed on Dec. 15, 2011 and mailed on Jan. 12, 2012; 3 pages.

International Search Report corresponding to European Application No. EP 06 00 4598, completed on Jun. 22, 2006; 2 pages.

International Search Report corresponding to European Application No. EP 06 01 6962.0, completed on Jan. 3, 2007 and mailed on Jan. 11, 2007; 10 pages.

International Search Report corresponding to International Application No. PCT/US05/36740, completed on Feb. 20, 2007 and mailed on Mar. 23, 2007; 8 pages.

International Search Report corresponding to International Application No. PCT/US2008/002981, completed on Jun. 9, 2008 and mailed on Jun. 26, 2008; 2 pages.

International Search Report corresponding to European Application No. EP 08 25 1779, completed on Jul. 14, 2008 and mailed on Jul. 23, 2008; 5 pages.

(56) References Cited

OTHER PUBLICATIONS

International Search Report corresponding to European Application No. EP 08 25 1989.3, completed on Mar. 11, 2010 and mailed on Mar. 24, 2010; 3 pages.
International Search Report corresponding to European Application No. EP 10 25 0715.9, completed on Jun. 30, 2010 and mailed on Jul. 20, 2010; 3 pages.
International Search Report corresponding to European Application No. EP 05 80 4382.9, completed on Oct. 5, 2010 and mailed on Oct. 12, 2010; 3 pages.
International Search Report corresponding to European Application No. EP 10 25 1437.9, completed on Nov. 22, 2010 and mailed on Dec. 16, 2010; 3 pages.
International Search Report corresponding to European Application No. EP 09 25 2897.5, completed on Feb. 7, 2011 and mailed on Feb. 15, 2011; 3 pages.
International Search Report corresponding to European Application No. EP 10 25 0642.5, completed on Mar. 25, 2011 and mailed on Apr. 4, 2011; 4 pages.
Extended European Search Report corresponding to EP No. 12 19 1035.0, completed Jan. 11, 2013 and mailed Jan. 18, 2013; 7 pages.
Extended European Search Report corresponding to EP No. 12 18 6175.1, completed Jan. 15, 2013 and mailed Jan. 23, 2013; 7 pages.
Extended European Search Report corresponding to EP No. 12 19 1114.3, completed Jan. 23, 2013 and mailed Jan. 31, 2013; 10 pages.
Extended European Search Report corresponding to EP No. 12 19 2224.9, completed Mar. 14, 2013 and mailed Mar. 26, 2013; 8 pages.
Extended European Search Report corresponding to EP No. 12 19 6911.7, completed Apr. 18, 2013 and mailed Apr. 24, 2013; 8 pages.
Extended European Search Report corresponding to EP 12 19 1035.0, completed Jan. 11, 2013 and mailed Jan. 18, 2013; 7 pages.
Extended European Search Report corresponding to EP 12 19 6904.2, completed Mar. 28, 2013 and mailed Jul. 26, 2013; 8 pages.
Extended European Search Report corresponding to EP 12 19 8749.9, completed May 21, 2013 and mailed May 31, 2013; 8 pages.
Extended European Search Report corresponding to EP 07 00 5812.5, completed May 13, 2013 and mailed May 29, 2013; 7 pages.
Extended European Search Report corresponding to EP 12 19 8776.2, completed May 16, 2013 and mailed May 27, 2013; 8 pages.
Extended European Search Report corresponding to EP 13 15 6297.7, completed Jun. 4, 2013 and mailed Jun. 13, 2013; 7 pages.
Extended European Search Report corresponding to EP 13 17 3985.6, completed Aug. 19, 2013 and mailed Aug. 28, 2013; 6 pages.
Extended European Search Report corresponding to EP 13 17 3986.4, completed Aug. 20, 2013 and mailed Aug. 29, 2013; 7 pages.
Extended European Search Report corresponding to EP 13 17 7437.4, completed Sep. 11, 2013 and mailed Sep. 19, 2013; (6 pp).
Extended European Search Report corresponding to EP 13 17 7441.6, completed Sep. 11, 2013 and mailed Sep. 19, 2013; (6 pp).
Extended European Search Report corresponding to EP 07 86 1534.1, completed Sep. 20, 2013 and mailed Sep. 30, 2013; (5 pp).
Extended European Search Report corresponding to EP 13 18 3876.5, completed Oct. 14, 2013 and mailed Oct. 24, 2013; (5 pp).
Extended European Search Report corresponding to EP 13 17 1856.1, completed Oct. 29, 2013 and mailed Nov. 7, 2013; (8 pp).
Extended European Search Report corresponding to EP 13 18 0373.6, completed Oct. 31, 2013 and mailed Nov. 13, 2013; (7 pp).
Extended European Search Report corresponding to EP 13 18 0881.8, completed Nov. 5, 2013 and mailed Nov. 14, 2013; (6 pp).
Extended European Search Report corresponding to EP 13 17 6895.4, completed Nov. 29, 2013 and mailed Dec. 12, 2013; (5 pp).
Extended European Search Report corresponding to EP 13 18 2911.1, completed Dec. 2, 2013 and mailed Dec. 16, 2013; (8 pp).
Extended European Search Report corresponding to EP 10 25 1795.0, completed Dec. 11, 2013 and mailed Dec. 20, 2013; (6 pp).
Extended European Search Report corresponding to EP 13 18 7911.6, completed Jan. 22, 2014 and mailed Jan. 31, 2014; (8 pp).

\* cited by examiner

MECHANICALLY TUNED BUTTRESS MATERIAL TO ASSIST WITH PROPER FORMATION OF SURGICAL ELEMENT IN DISEASED TISSUE

CROSS REFERENCE TO RELATED PATENT APPLICATIONS

The instant patent application claims priority to U.S. Provisional Patent Application Ser. No. 60/764,451 and U.S. Provisional Patent Application Ser. No. 60/764,449 both to Michael A. Soltz filed on Feb. 2, 2006 which are both herein incorporated by reference in their entirety. The instant patent application also incorporates by reference U.S. patent application Ser. No. 11/409,154 to Michael A. Soltz entitled "Method and System to Determine an Optimal Tissue Compression Time to Implant a Surgical Element" filed contemporaneously with the instant patent application.

BACKGROUND

1. Technical Field

The present disclosure is directed to surgical stapling devices and sutures and, in particular, a buttress device used in connection or in combination with a surgical instrument for ensuring that an optimal amount of tissue compression is applied to tissue for an optimal formation of staples and sutures. Even more particularly, the present disclosure is directed to a buttress device that provides a visual indication to the surgeon that the optimal amount of tissue compression has been reached, and that it is the proper time to apply the surgical element.

2. Description of the Related Art

Anastomosis is the surgical joining of separate hollow organ sections. Typically, an anastomotic procedure follows surgery in which a diseased or defective section of hollow tissue is removed. Thereafter, the procedure has the steps that the remaining end tissue sections are to be joined. Depending on the desired anastomotic procedure, the end sections may be joined by either circular, end-to-end, end-to-side, or side-to-side organ reconstruction methods.

In a known circular anastomosis procedure, two ends of organ sections are joined by a stapling device. The stapling device can drive a circular array of staples through the end of each organ section. The device can simultaneously core any tissue interior of the driven circular array of staples to free a tubular passage. Many examples for performing circular anastomosis of hollow organs are described in U.S. Pat. Nos. 6,959,851, 6,053,390, 5,588,579, 5,119,983, 5,005,749, 4,646,745, 4,576,167, and 4,473,077, which are incorporated by reference herein in their entirety.

Typically, these devices include an elongated shaft having a handle portion at a proximal end thereof to effect actuation of the device. The device also has a staple holding component disposed at a distal end thereof. An anvil assembly including an anvil rod with an attached anvil head is mounted to the distal end of the device. The anvil is adjacent a staple holding component. Opposed end portions of tissue of the hollow organ(s) to be stapled are clamped between the anvil head and the staple holding component. The clamped tissue is stapled by driving one or more staples having a predetermined size from the staple holding component. In this manner, the ends of the staples pass through the tissue and are deformed by the anvil head. An annular knife is advanced to core tissue within the hollow organ. In this manner, the knife frees a tubular passage within the organ.

Surgical stapling devices for performing circular anastomosis have also been used to treat internal hemorrhoids in the rectum. During the use of a circular stapling device for hemorrhoid treatment, the anvil head and the staple holding component of the surgical stapling device are inserted through the anus and into the rectum with the anvil head and the staple holding component in an open or un-approximated position. Thereafter, a suture is used to pull the internal hemorrhoidal tissue and/or mucosal tissue towards the anvil rod. Next, the anvil head and the staple holding component are approximated to clamp the hemorrhoidal tissue and/or mucosal tissue between the anvil head and the staple holding component. The stapling device is fired to remove the hemorrhoidal tissue and/or mucosal tissue and staple the cut tissue. Sutures are also known in the art to connect or join tissue. Although the use of circular anastomosis staplers for hemorrhoid treatment has many benefits often, a surgeon will encounter, over the course of a surgical procedure, one or more different types of tissue in the body for which to apply a surgical element such as a staple.

Non-circular stapling devices are also known in the art. In endoscopic or laparoscopic procedures, surgery is performed through a small incision or through a narrow cannula inserted through a small entrance wound in the skin. In order to address the specific needs of endoscopic and/or laparoscopic surgical procedures, endoscopic surgical stapling devices have been developed and are disclosed in, for example, U.S. Pat. No. 5,040,715 (Green, et al.); U.S. Pat. No. 5,307,976 (Olson, et al.); U.S. Pat. No. 5,312,023 (Green, et al.); U.S. Pat. No. 5,318,221 (Green, et al.); U.S. Pat. No. 5,326,013 (Green, et al.); U.S. Pat. No. 5,332,142 (Robinson, et al.); and U.S. Pat. No. 6,241,139 (Milliman et al.), the entire contents of each of which are incorporated herein by reference. These non-circular or linear stapling devices are useful for gastrointestinal or bariatric surgery and include a staple cartridge and an anvil for applying titanium surgical staples into the body to join or connect tissue sections to one another.

Some other tissue types include cardiac tissue, colorectal tissue, gastrointestinal tissue, and pulmonary tissue. In these different types of tissues, there may be a number of different other types of classes of such tissue, such as ischemic tissue, or diseased tissue, thick tissue, tissue treated with medicines or compounds, diabetic tissue, as well as numerous others. However, one of ordinary skill in the art should appreciate that the present disclosure is not limited to diseased tissue.

It is desired to ensure proper formation of the respective surgical element (such as the array of staples) into such tissue. It has been observed that with certain types of tissue such as ischemic tissue, or diabetic tissue an amount of compression can be applied to the tissue for an optimal time period to assist the instrument.

However, further compression for a time period (after an optimal time period) is not favored. In the surgical environment, it is difficult to visually appreciate the optimal amount of compression that should be applied to the various tissue types, and also it is difficult to visually appreciate the optimal time period for tissue compression. It should be appreciated that tissue compression is not limited to diseased tissue, and it is envisioned that compression may be applied to other instances where non-diseased tissue is encountered in the surgical procedure to ensure a positive surgical outcome.

Accordingly, a continuing need exists in the art for a device that provides an indication to the surgeon that a threshold compression has been reached and that the surgical element should be applied to the tissue (such as a staple).

A continuing need exists in the art for a device that is used in connection with a surgical instrument that can act as an intermediary between the instrument and the tissue so the tissue is optimally compressed by the intermediary for proper formation of the surgical element such as a staple without damaging the tissue. There is also a need for a material that can support thin diseased tissue during stapling so the compression cannot damage the tissue. There is also a need in the art for a device that can reinforce a staple line and to redistribute the pressure gradient that forms the staple line more evenly over an area of the healthy or diseased tissue.

SUMMARY

According to a first aspect of the present disclosure, there is provided a surgical indicator to indicate the proper formation of a surgical element. The indicator has a member having a modulating property. The member modulates to a first condition when no stress is applied, modulates to another second condition when a stress is applied. The modulating property is configured to provide an indication when compressed to a predetermined compression stress level. The predetermined compression stress level indicates an optimal tissue compression of the tissue type. The indication is a tissue state that is optimal for the formation of the surgical element for the predetermined tissue type.

The indication is not limited to a pre-firing indication and can also be an indication of a post firing condition. The substrate may remain connected to the operative site at the conclusion of the firing of the surgical instrument. Thus, the substrate having the indication remains on the substrate, and the surgeon can inspect the indication at any time after the firing. The substrate can thus also provide an indication of the compression that was applied to the tissue at the firing at a time period long after that firing of the instrument.

According to another aspect of the present disclosure there is provided an apparatus for determining an optimal amount of tissue compression prior to the insertion of a surgical element into the tissue. The apparatus has a substrate made from a predetermined material. The predetermined material has an initial color when no stress is applied to the substrate. The predetermined material also has second color when a predetermined compression stress is applied to the substrate. The second color indicates a proper time in order to fire a surgical element into tissue.

According to yet another aspect of the present disclosure there is provided an apparatus for supporting tissue during compression prior to the insertion of a surgical element into the tissue. The apparatus has a substrate made from a predetermined material. The predetermined material has a thickness and a predetermined stress-strain profile. The predetermined stress-strain profile is complementary to a stress-strain profile of the tissue to permit the substrate to support the tissue when the surgical element is delivered into the tissue. The substrate provides hemostasis control of the tissue when the surgical element is delivered into the tissue. The substrate can be made of collagen, degradable polymers, or polysaccharides. In one embodiment, the substrate may have multiple layers or be a composite material having a support layer and a web layer. The substrate may have a collagen support layer and a web that provides support and resiliency to the collagen support layer.

According to a further aspect of the present disclosure there is provided a method of determining an optimal amount of compression of tissue. The method provides an indication to the surgeon of the optimal compression and a time to fire a surgical element into tissue. The method has the steps of applying a pressure sensitive film to tissue. In another alternative embodiment, the method may have the steps of applying a pressure sensitive foam, a film having particles, a gel, an adhesive or a combination thereof to tissue as a diagnostic device to provide the indication. The pressure sensitive film is configured to provide an indication when compressed to a predetermined compression stress level. The film is tuned such that the predetermined compression stress level indicates the optimal tissue compression of the tissue type. The method has the steps of compressing the pressure sensitive film and the tissue and firing the instrument when the pressure sensitive film provides a visual indication of the optimal compression.

According another aspect of the present disclosure there is provided a method of determining an optimal amount of compression of tissue to provide an indication to the surgeon of the optimal compression and a time to fire a surgical element into tissue. The method has the step of applying a substrate having a dye filled sac having a reservoir. The sac is configured to burst or rupture when compressed to a predetermined compression stress level. The sac is configured to yield when the predetermined stress level is the optimal tissue compression of the tissue type. The method also has the step of compressing the substrate together with the tissue and firing the instrument when the dye is released from the sac. The dye can be a colorant, or a pigment, or further include a biochemical probe all of which may be colored or emit color upon excitation by low energy radiation.

In one embodiment, the substrate may have a dye filled sac that has a certain color. The colored dye will be released from the sac once the sac ruptures and permit the surgeon to visually appreciate that the optimal compression has been reached. In another embodiment, the sac may have a predetermined chemical in the sac. Once the predetermined compression is reached, the predetermined chemical is released and can react with the substrate or another material to change color once the sac ruptures. This chemical reaction permits the surgeon to instantly visually appreciate that the optimal compression has been reached.

In yet another embodiment of the present disclosure, the substrate may be formed with a plurality of liquid crystals. The liquid crystals are made with the substrate and can be cast in place when the substrate is manufactured. In one embodiment, the liquid crystals are cast into a polymeric material and the polymeric substrate is extruded from a die. The liquid crystals have a predetermined initial state and a second state when compressed with the optimal amount of compression. Once the predetermined compression is reached in the procedure and applied to the substrate having the plurality of liquid crystals, the liquid crystals can change an optical property of at least one of the liquid crystals and the substrate in response to the compression to provide the indication. This indication permits the surgeon to instantly visually appreciate that the optimal compression has been reached.

In still another embodiment of the present disclosure, the substrate may be formed with a plurality of microspheres. The microspheres are manufactured with the substrate to include a material. In one embodiment, the microspheres have a size that is of an order smaller relative to the sacs of the previous embodiment. Once the predetermined compression is reached in the procedure and applied to the substrate having the microspheres, the microspheres can rupture to release their contents and provide an indication in response to the compression. This indication permits the surgeon to instantly visually appreciate that the optimal compression has been reached.

In still a further embodiment of the present disclosure, the substrate may be formed with a plurality of nano-spheres. The nano-spheres are manufactured with the substrate to include a material in a lumen formed in each of the nano-spheres. In one embodiment, the nano-spheres have a minuscule size relative to the sacs of the previous embodiment. Once the predetermined compression is reached in the procedure and applied to the substrate having the nano-spheres, the nano-spheres can rupture to release their contents and provide an indication in response to the compression. This indication permits the surgeon to instantly visually appreciate that the optimal compression has been reached. Each of the nano-spheres can rupture at different stress gradients to provide a number of different indications depending on the specific encountered compression in the procedure.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
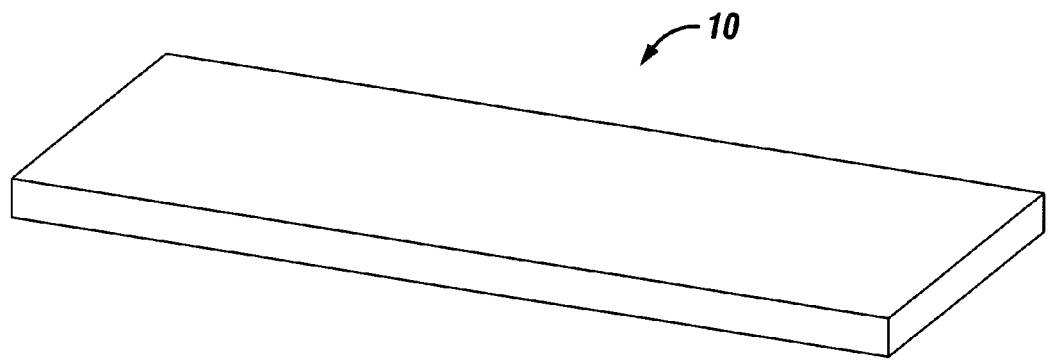
FIG. 1 is a perspective view of a mechanically tuned buttress material to support tissue for surgical stapling.

Embodiments of the presently disclosed buttress materials will be described herein below with reference to the accompanying drawing figures wherein like reference numerals identify similar or identical elements. In the following description, well-known functions or constructions are not described in detail to avoid obscuring the disclosure in unnecessary detail.

Figure 2:
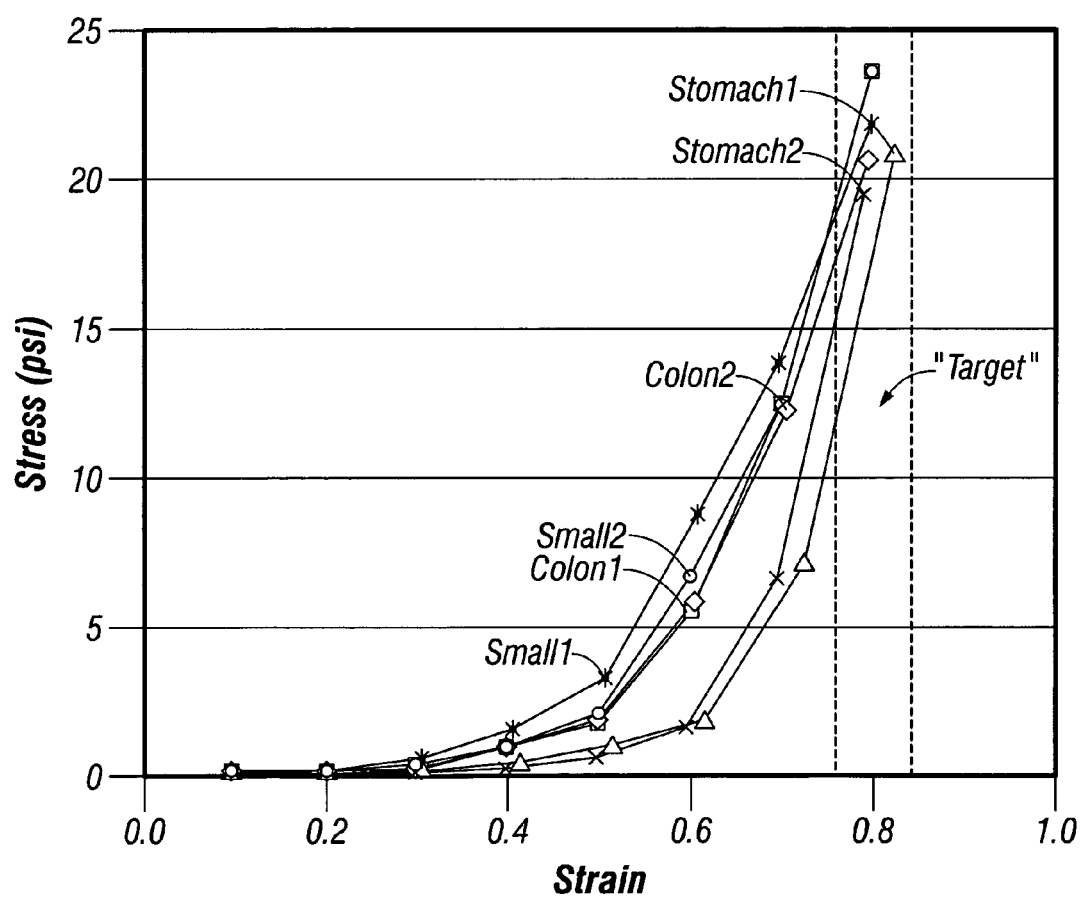
FIG. 2 is a graph of an equilibrium stress plotted against an amount of strain for a number of different tissue types to determine a tissue mechanical property for the buttress material of FIG. 1.

Referring now to FIG. 1, there is shown an embodiment of the buttress material 10 of the present disclosure. In one embodiment, a moveable and a stationary platen (not shown) may be used in order to compress tissue to assist with application of the surgical element into tissue. The present disclosure is intended to be used with any stapling device known in the art, and reference to any particular type of stapling devices is simply for illustration only and should not be construed to limit the present disclosure. The tissue may be any gastrointestinal tissue, abdominal tissue, pulmonary tissue, colonic tissue, cardiac tissue, muscle or any other mammalian tissue where stapling and sutures may be applied for therapeutic treatment. Properties of the tissue can be determined by either static or dynamic testing. Referring to FIG. 2, the stretch ($\lambda$) is defined as a ratio of the deformed thickness of the tissue to an undeformed thickness as shown below wherein $h_f$ is the final height of the tissue and $h_i$ is the initial height of the tissue:

$$\lambda = \frac{h_f}{h_i}$$

Stress ($\sigma$) is defined as the force (f) divided by the contact area (A) of the loading platen.

$$\sigma = \frac{F}{A}$$

The strain is derived from the stretch (λ) and is equal to 1 minus the stretch (λ). As shown in FIG. 2, the stress in pounds per square inch is plotted on the y-axis and the strain is plotted on the x-axis. As can be understood from the graph, there is shown a number of stress strain profiles for each of the different tissue types including a first and a second stomach tissue, a first and second colonic tissue, and a first and second small intestinal tissue. As the tissue undergoes stress and strain the optimal target operating conditions for strain and stress are located in the target zone. The target zone indicates an optimal amount of stress and strain for hemostasis control and for optimal healing of the tissue as indicated by the target rectangle shown in dotted lines for illustration purposes in FIG. 2. As stress is equal to a modulus of elasticity times the strain, it is appreciated that as stress increases for each of the discrete tissue samples, the modulus of elasticity remains constant to a certain threshold and then will also change when undergoing stress in excess of the threshold. It is appreciated that the modulus is fixed within a range, but then the modulus will vary after a certain predetermined threshold such as when the tissue undergoes intense stress.

In one embodiment, the buttress material 10 is made to have substantially the same stress-strain profile as the tissue with which it is to be used or having substantially the same modulus and profile as shown in FIG. 2. The buttress material 10 may be made of one or more polymers. The one or more polymers may be a synthetic or a natural material. Some of the materials that the buttress material 10 may be made from include polymers polyorthoesters, lactones, lactone copolymers, polysaccharides, detran, cellulose, hyaluronic acid, CMC, alginate, proteins, collagen, gelatin, keratin, elastin, silk, vinyl polymers, silicones, silicanes copolymers, polyurethanes, permanent polyurethanes, degradable polyurethanes, polyamines, polyamides, polyesters, polyether esters, polysulfine, polyalkelene oxides, PEG, peos, pey-ppgs, amorphous polymers, crystalline polymers, liquid crystal polymers, conducting polymers, fluorescent polymers, actuating polymers, anti-fluorescent polymers, and any combinations thereof. Some others of which may provide a diagnostic capability as will be discussed further detail below also including a liquid crystalline polymer, a conducting polymer, or an actuating polymer.

The stiffness of the polymer is controlled to have substantially the same stress-strain profile as the tissue. In one embodiment, the polymer has modified structural fibers to have substantially the same stress-strain profile as the tissue. Alternatively, if the buttress material 10 is a composite structure or is a multilayered structure, one of the layers of the buttress material 10 may include a mesh or mesh like material in order to provide support to the composite or multi-layered structure. In another embodiment, the polymer has modified structural fibers that are controlled by a degree of cross-linking of the fibers to have the substantially same stress-strain profile as the tissue. In yet another embodiment, the polymer may simply be selected from a number of existing polymers to substantially match the stress-strain profile as the tissue. One of skill in the art should appreciate that the surgeon would apply the surgical element through the tissue sections to join the tissue sections together and would also join the surgical element through the buttress material 10 shown in FIG. 1.

Figure 3:
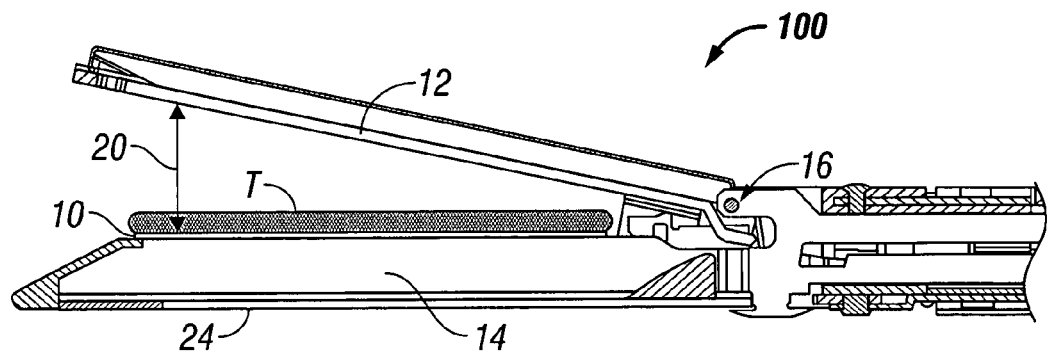
FIGS. 3 and 4 are cross-sectional views of a surgical stapler compressing tissue with the mechanically tuned buttress material supporting the tissue according to the present disclosure.
Figure 4:
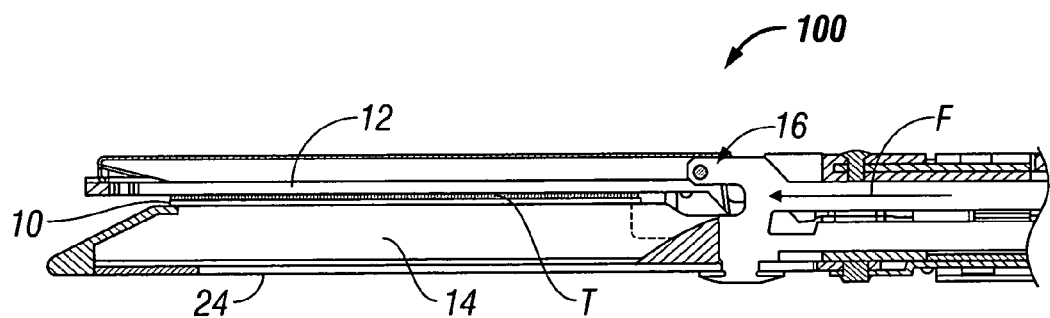

A movable platen and a stationary platen may have numerous configurations to apply compression to the tissue, however for the purposes of illustration, the compression to the tissue T is applied from a surgical stapler as shown in FIGS. 3 through 4. Referring now to FIG. 3, the surgical stapler 100 is shown having an anvil 12 and a staple cartridge 14 with an anvil drive assembly 16. The anvil drive assembly 16 is advanced distally to contact an anvil 12 to close the stapler 10 as shown in FIG. 4, and to provide compression to the tissue T disposed within the gap 20 between the anvil 12 and the lower jaw 24. It is envisioned that many other stapler assemblies can be used with the present disclosure including an anastomosis device such as the instrument that is described in U.S. Pat. No. 6,959,851 which has been previously incorporated by reference.

Some surgeons will use sutures instead of staples when treating ischemic tissues. Accordingly, the present disclosure provides for a material to support and reinforce the tissue in order to apply a surgical instrument through the tissue with proper formation of the surgical element to ensure a proper surgical outcome.

FIG. 3 shows a tissue T between the anvil 12 and a second stationary jaw 24 with a buttress material 10 disposed therebetween. The buttress material 10 provides support and reinforcement to the tissue T so the surgeon can compress the tissue T and apply the surgical element such as a staple through the tissue T to join the tissue to another second tissue or section and to assist with a proper and repeated formation of the surgical element.

Figure 5:
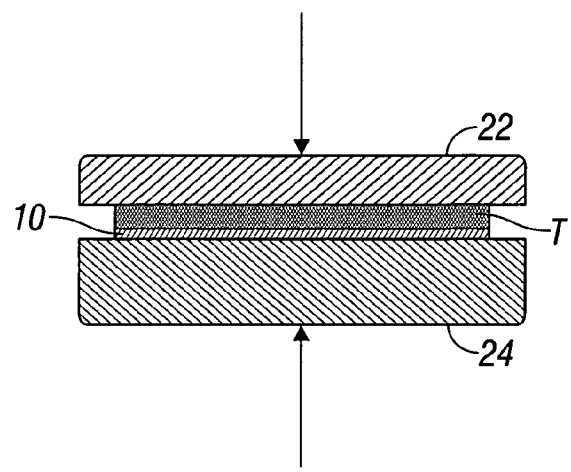
FIG. 5 shows an upper jaw and a lower jaw compressing tissue with the mechanically tuned buttress material supporting the tissue according to the present disclosure.

Thus, by compressing the tissue, the surgeon has an amount of buttress material 10 having a complementary compressive property relative to the tissue T. The buttress material 10 reinforces the tissue T when applying compression to the tissue. Referring to FIG. 4, and the cross sectional view in FIG. 5, once the proper amount of compression is reached, the surgeon can fire the instrument. The surgeon can apply the surgical element such as a staple through the tissue T to ensure proper formation of the surgical element without damaging the tissue. In other words, the buttress material 10 would exhibit low stress under low compression values, and the buttress material 10 would exhibit high stress under higher compression values to match the tissue T, and provide a support to the tissue as if the surgeon were not simply firing through thin ischemic tissue T, but instead were firing the stapler through normal thick and well defined tissue T. It should be appreciated that the compression ranges for the particular buttress material 10 in this embodiment would be complementary to the stress-strain profile of the individual tissue type as shown in FIG. 2. The compression ranges would depend on the stress-strain curve that equates to a predetermined pressure on the tissue. Ideally, the modulus of elasticity of the buttress material 10 would match the modulus of elasticity of the specific tissue shown in FIG. 2.

Figure 6:
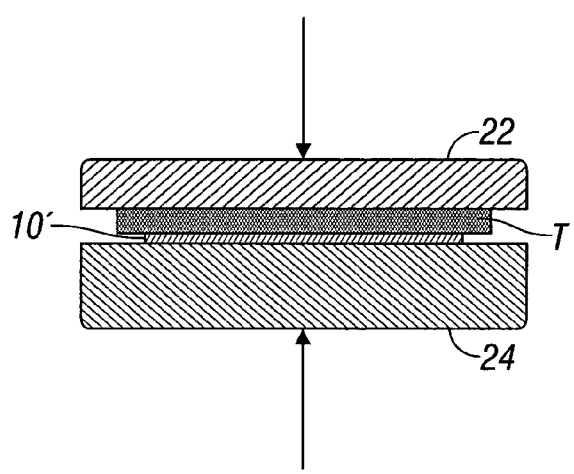
FIG. 6 shows another embodiment with an upper jaw and a lower jaw compressing tissue with the mechanically tuned buttress material stiffer than the tissue.

In another embodiment, shown in FIG. 6, the buttress material 10' has a different property relative to the tissue T. In this embodiment, the buttress material 10' yields at a greater rate relative to the tissue T when the compressive stress is applied by the jaws 22, 24. Again, when compressing the tissue T, the surgeon has an amount of buttress material 10' to reinforce the tissue T when applying the compression force to the tissue. In this embodiment, the buttress material 10' is softer than the tissue T and would compress and yield more than the tissue T when the force is applied and thereby provide additional compliance. Accordingly, once the proper amount of compression is reached, the surgeon could apply the surgical element such as a staple through the tissue T to assist with proper formation of the surgical element without damaging the tissue T. It should be appreciated that the compression ranges for the particular buttress material 10' in this embodiment would also be derived from the stress-strain profile of the individual tissue type as shown in FIG. 2. The compression ranges would depend on the stress-strain curve that equates to a predetermined pressure on the tissue. Ideally, the modulus of elasticity of the buttress material 10' would be more elastic than the modulus of elasticity of the specific tissue shown in FIG. 2.

Figure 7:
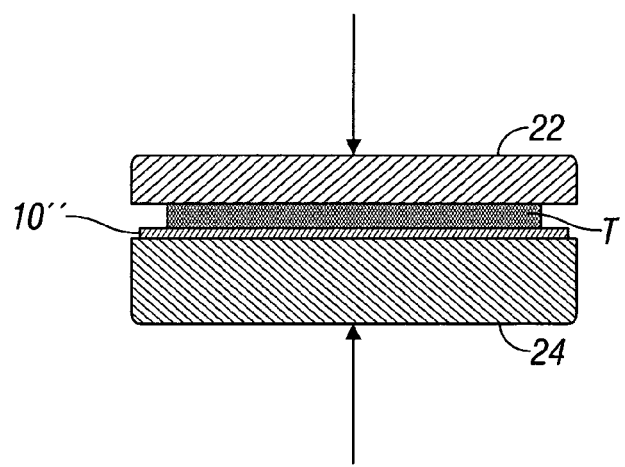
FIG. 7 shows another embodiment with an upper jaw and a lower jaw compressing tissue with the mechanically tuned buttress material softer than the tissue.

In another embodiment, shown in FIG. 7, the buttress material 10" again has a different property relative to the tissue. In the embodiment shown in FIG. 7, the buttress material 10" does not yield at a greater rate relative to the tissue T when the compressive stress is applied by the jaws 22, 24, and instead is stiffer than the tissue T.

Again, when compressing the tissue T, the surgeon has an amount of buttress material 10" to reinforce the tissue T when applying the compression to the tissue T. In this embodiment, the buttress material 10" is more rigid than the tissue T. As opposed to the embodiment of FIG. 6, here the buttress material 10" would resist compression and yielding relative to the tissue. The buttress material 10" would compress less than the tissue T when the force is applied and thereby transfer the compressive force to the tissue T. This transfer assists with hemostasis control of the tissue T. Accordingly, once the proper amount of compression is reached, the surgeon could apply the surgical element such as a staple through the tissue to assist with proper formation of the surgical element with repeatability and without damaging the tissue, and further provide hemostasis control of the tissue. It should be further appreciated that the compression ranges for the particular buttress material 10" in this embodiment would also be derived from the stress-strain profile of the individual tissue type as shown in FIG. 2 such as small intestinal tissue, colonic tissue, and stomach or abdominal tissue. The compression ranges would depend on the stress-strain curve that equates to a predetermined pressure on the tissue. Ideally, the modulus of elasticity of the buttress material 10" would be less elastic or stiffer than the modulus of elasticity of the specific tissue shown in FIG. 2.

Figure 8:
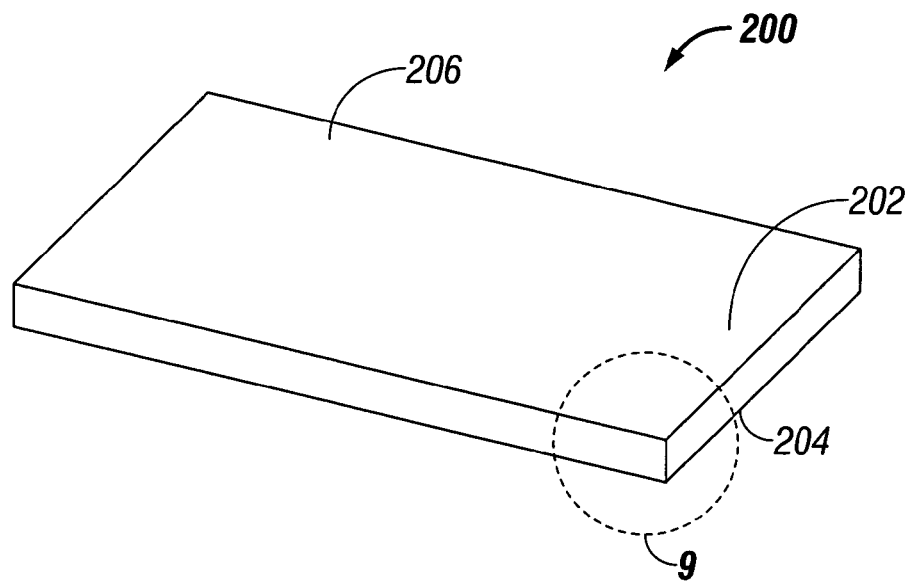
FIG. 8 is a perspective view of a buttress material for supporting the tissue according to the present disclosure with the buttress material adapted to provide a visual indication to the surgeon that the optimal amount of compressive stress has been reached.
Figure 9:
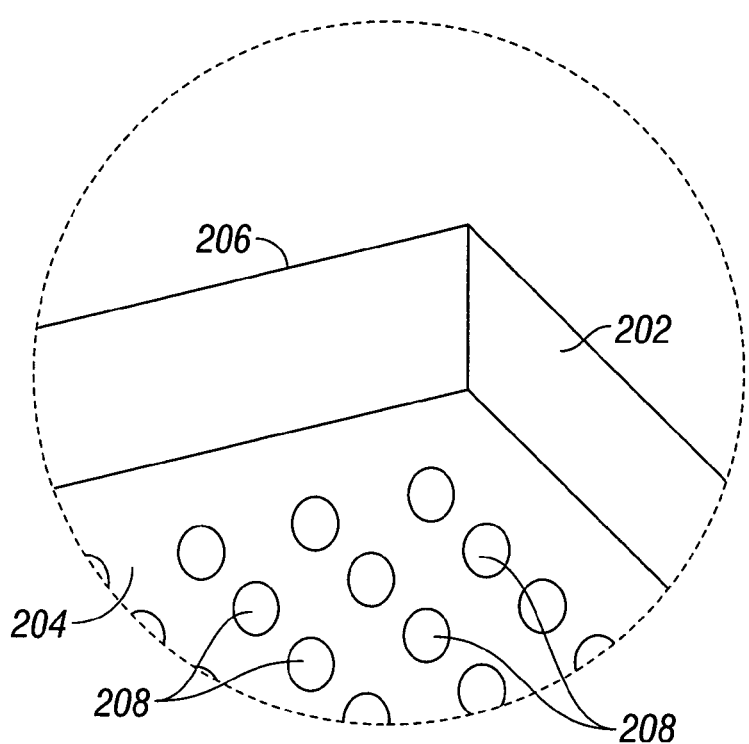
FIG. 9 is an enlarged area of detail of an embodiment of the distal side of the buttress material having a number of dye filled sacs.
Figure 10:
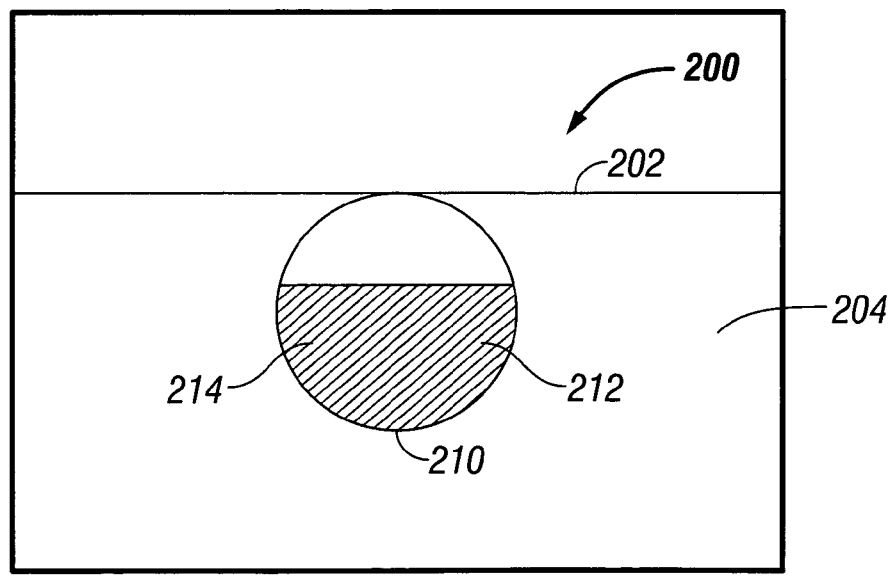
FIG. 10 is an enlarged view of a sac of FIG. 9.

Referring now to FIGS. 8 through 10, there is shown another alternative embodiment of the present disclosure. In this embodiment, the system has a mechanically tuned buttress material 200. The mechanically tuned buttress material 200 is made from a natural or synthetic material, and has a substrate 202. The mechanically tuned buttress material 200 may be arranged in a number of predetermined mechanically tuned constructions with each different construction suitable to be used with a particular diseased tissue or a specific tissue type. Each mechanically tuned material is suitable for use with different diseased or tissue types such as thin tissue, diabetic tissue, ischemic tissue or other types of tissue such as gastrointestinal, cardiac tissue, pulmonary tissue or anther tissue type.

However, in this embodiment each mechanically tuned buttress material 200 provides the surgeon with a visual indication of a threshold amount of compression that is to be applied to the tissue for a predetermined time period. Once the visual indication is communicated, the surgeon will visually know that it is the proper time to implant the surgical element in the tissue. The surgeon will be provided with an indication that it is time for joining the two tissue sections together and thus will release the tissue after firing the instrument and no longer apply any further compression to the tissue. Thus, the mechanically tuned buttress material 200 provides for an optimal compression of tissue prior to introducing the surgical element into tissue.

It should be appreciated that with the buttress material 200 fixed to the tissue, the buttress material 200 may be inspect later long after the firing of the instrument in post operative care. The surgeon may inspect the tissue adjacent the buttress material 200 to ensure healing of the tissue, and that the proper amount of compression was applied to ensure a positive surgical outcome.

The substrate 202 can be made from a polymer. The polymer can be the same as or different from the polymers listed above for the buttress material 10, and may include the previously discussed diagnostic capability. As indicated previously, the polymers can include liquid crystal polymers, conducting polymers, fluorescent polymers, actuating polymers, anti-fluorescent polymers, and any combinations thereof. Some of the polymers forming the substrate 202 may have other mechanical properties that can provide the indication exclusive of any stress applied to the polymer. The polymer itself can include one or more mechanical properties that can contribute to providing the indication that include a molecular weight, a polydispersity index, a thermal property or history, a monomer structure, a monomer selection, a cross linking density, a viscoelasticity property of the polymer, or a stability of the polymer. Various configurations are possible and within the present disclosure.

The substrate 202 may be made from any suitable flexible material that can be bent, or wrapped around tissue without damaging the tissue or abrading the tissue. The substrate 202 is made from a biocompatible material, and can be readily applied and removed from the inner tissues of the body such as gastrointestinal tissue, cardiac tissue, colonic tissue, small intestinal tissue, large intestinal tissue and pulmonary tissue without abrading the tissue, and/or harming the tissue.

The substrate 200 has a distal surface 204 that contacts the tissue and also has an opposite proximal surface 206. In one embodiment, the substrate 202 may be made from a pressure sensitive film. In another embodiment, the substrate 202 may be made from a pressure sensitive gel, pressure sensitive foam, a material having a number of particles, or adhesives and any combinations thereof. Once an optimal amount of stress is applied to the substrate 202, the substrate 202 will modulate to provide a visual indication to the surgeon that a certain compression threshold has been achieved. The visual indication may be a change in one or more optical properties of the substrate 202 or a change in a visual state from a first condition to another second different condition.

Figure 8A:
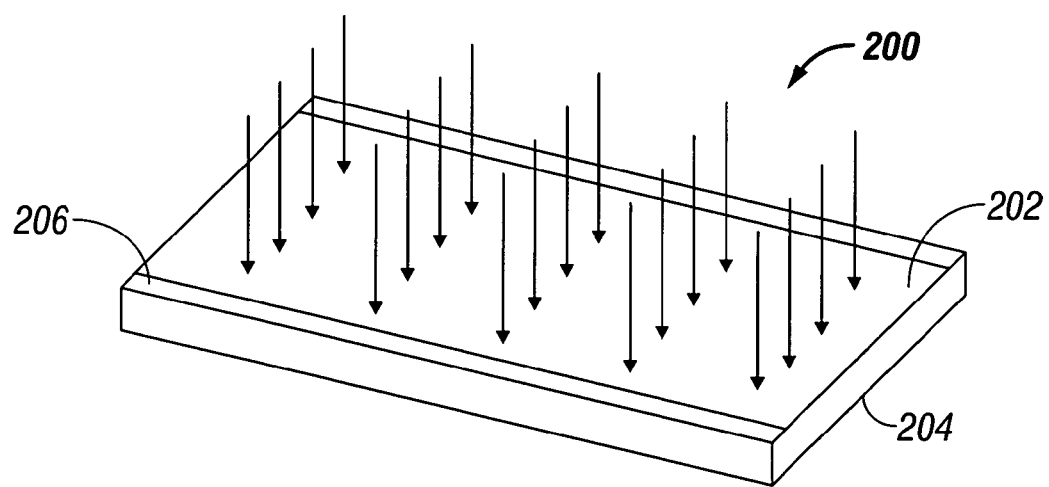
FIG. 8A is a perspective view of the buttress material of FIG. 8 providing a visual indication to the surgeon that the optimal amount of compressive stress has been reached.

In one embodiment, the change in a visual state to provide the indication may be from translucent condition of the substrate 200 to an opaque condition of the substrate 200. In another embodiment, the change in the visual state may be from a first color to a second color. Various configurations are possible. In one embodiment, the indication may be from one initial color to a second color as shown in FIG. 8A. The second color will provide the surgeon with an indication that the optimal compression threshold has been reached for the specific tissue, and that the tissue is ready for introduction of a surgical element such as a number of staples.

In another embodiment, the substrate 202 is not made from a pressure sensitive film and instead has a number of sacs 208 shown in FIG. 9. The sacs 208 have a predetermined tensile strength or burst strength that is engineered to rupture or burst at a specific pressure when the substrate is compressed. In one embodiment, the sacs 208 are arranged on the distal surface 204 of the substrate 202. In another embodiment, the sacs 208 may be placed in the interior of the substrate 202 and be confined within the interior of the substrate 202.

Referring to FIG. 10, there is shown a view looking at the distal side of the substrate 204. The sacs 208 have an outer surface 210, and an inner lumen 212 that is sealed from the outer environment. The sacs 208, in one embodiment, may be formed in a discrete array of rows on the distal surface of the substrate 202 such as ten by ten, or twenty by twenty. In another embodiment, the sacs 208 may be in predetermined clusters on the distal side 204 of the substrate 202 or alternatively in the interior space of the substrate 202. In still another embodiment, the sacs 208 may be dimensioned so as to encompass the entire distal side 204 of the substrate 202. Various configurations and possible and depend on the surgical element applied to join the tissue and the tissue type. The sacs 208 of the substrate 202 may be made from a trimethyl carbonate, or a polysaccharide such as dextran. Alternatively, the sacs 208 can also be made from polyglycolic acid, or polylactic acid.

FIG. 10 shows one sac 208 of the substrate 202. The sacs 208 have an inner lumen 212 that is sized to cover a predetermined material within the inner lumen 212. In one embodiment, the inner lumen 212 is generally spherically shaped. In another embodiment, the inner lumen 212 may be generally orthogonal shaped or tubular, or in still a further embodiment, the inner lumen 212 may be irregularly shaped. Various inner lumen configurations and possible and depend on the surgical element being applied to join the tissue, the amount of compression, the contents of the lumen and the tissue type.

The predetermined material is a dye 214 that is in the inner lumen 212. The dye 214 may be a suture dye and is non-toxic and an amount of the dye 214 may enter the body without any toxic effect or harm to the tissue. The predetermined material may alternatively be a fluorescent dye, an ultraviolet dye, a visible dye, a pigment, or a color additive. In one embodiment, each individual sac 208 is set in advance in relation to a tissue type such as gastrointestinal tissue, cardiac tissue, pulmonary tissue, or muscle so the sacs 208 will all yield when a certain amount of compressive force is placed on the substrate 202 that matches the tissue type.

In one embodiment, the dyes 214 may be any ultra-violet visible dye (food colorant, etc) or probes such as fluorescent or infrared (IR)/near-IR probes. These probes may require a predetermined amount of excitation energy for emission. Further, the polymer composing the substrate or the particles could be prepared from, or functionalized with, the above mentioned "probe" molecules, in that the polymer provides both the mechanical and visualization properties. Some probes include a fluorescent probe, FTI flourescein, fluorescein isothiocyanate (FITC) and tetramethylrhodamine isothiocyanate (TRITC) probes, rhodamine, DAPI, a molecular probe such as a "nuclear yellow" probe, an acridine orange probe, DRAQ™ and SYTOX® nuclear labels, propidium iodide and other fluorophores with similar absorption and emission spectra.

Figure 11:
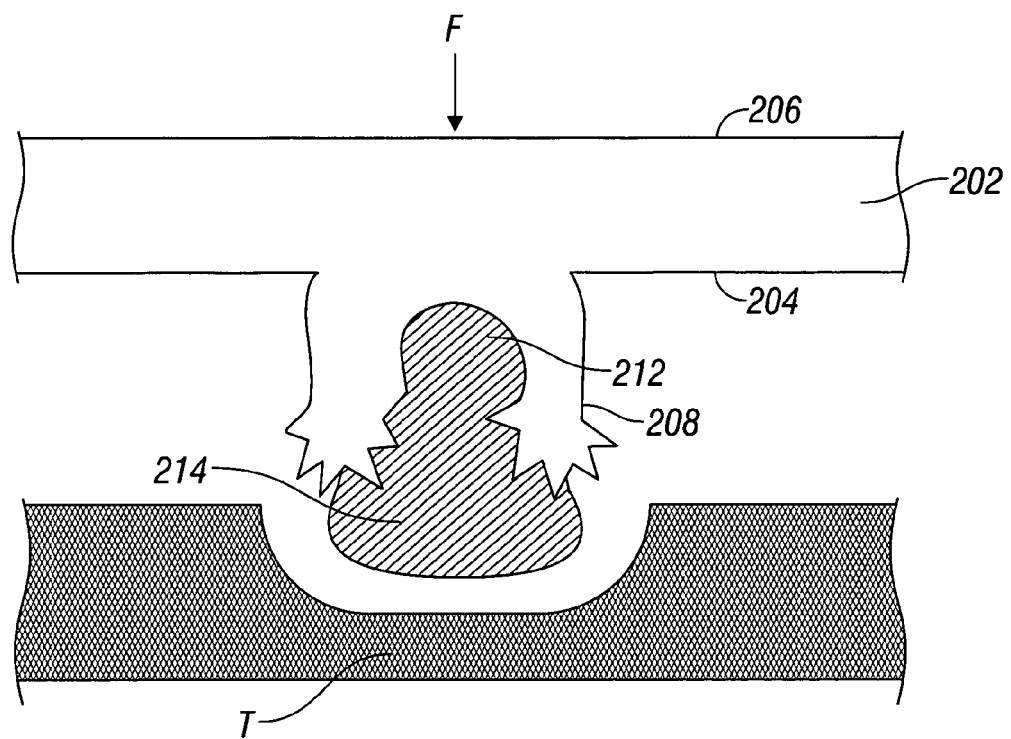
FIG. 11 is an enlarged area of detail of an embodiment of the distal side of the buttress material having a dye filled sac with the sac releasing the dye in response to the compression from the upper and lower jaws.

Referring now to FIG. 11, when compressed, the contents or dye 214 of the sacs 208 will escape from the substrate 202 and on to the tissue T. In another embodiment, when compressed, the contents or dye 214 of the sacs 208 will leak from the sacs 208 and be confined within the interior of the substrate 202 but be visible from the outside of the substrate 202, and will not contact the tissue. In this embodiment, the dye 214 cannot escape from the substrate 202, and other dye types can be used. As shown in FIG. 8A, in this manner, the surgeon will visually see a change in color at the desired site at the predetermined compression, and the surgeon will then know to apply the surgical element into the tissue T upon seeing the indication. In another embodiment, the substrate 202 may be formed with no dye 214. Instead, the inner lumen 212 will be empty and will simply audibly pop at the optimal compression. Here, the buttress material 200 will audibly indicate to apply the surgical element into the tissue T.

Alternatively, if the surgeon does not see or hear the indication, the surgeon will be provided with an alternative or false indication. The surgeon will know that the substrate 202 is not being applied with a compressive force in either a uniform manner or that an insufficient compressive force is being applied to the tissue T. In this instance, the surgeon can reorient the instrument, and attempt again to apply the surgical element at the desired site.

Moreover, if the surgeon after repeated attempts does not see the indication, surgeon will know that the substrate 202 is not being applied with a compressive force in either a uniform manner or that an insufficient compressive force is being applied to the tissue T. In this instance, the surgeon may then apply another different type of surgical element, such as a suture at the desired site.

Figure 11A:
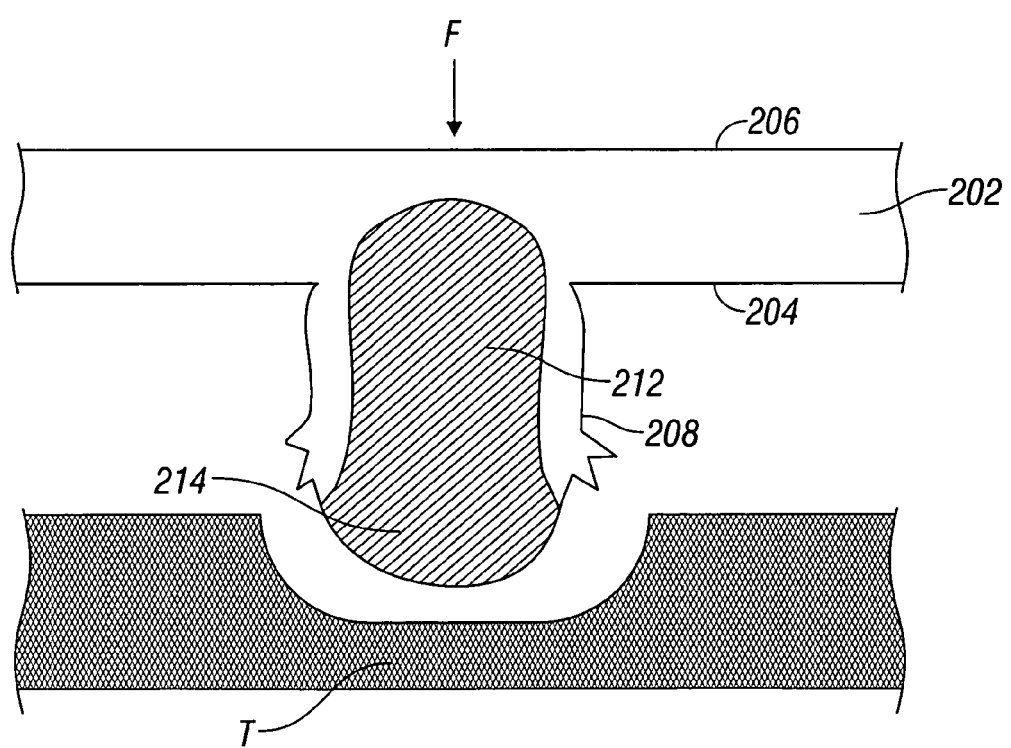
FIG. 11A is an enlarged area of detail of an embodiment of the distal side of the buttress material having a sac with a chemical reactant with the sac releasing the chemical reactant in response to the compression from the upper and lower jaws.

Referring now to FIG. 11A, there is shown an alternative embodiment of the substrate 202 of the present disclosure. In this embodiment, the substrate 202 does not have any dye as in FIG. 11 but instead has different contents. In this embodiment, the sac 208 has a chemical substance 214 disposed therein. Like the previous embodiments, the chemical substance 214 may escape from the substrate 202 when the sac 208 ruptures. However, in this embodiment, when compressed, the contents or chemical substance 214 of the sacs 208 will rupture and leak from the sacs 208 and will contact an exterior surface of the substrate 202.

Figure 11B:
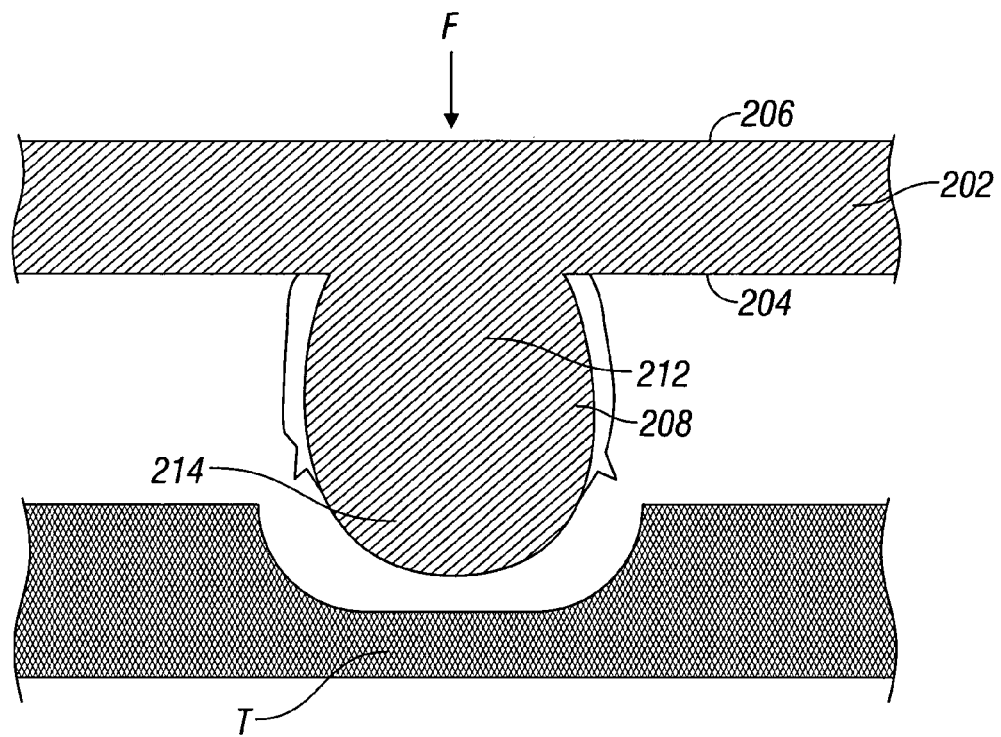
FIG. 11B is an enlarged area of detail of the embodiment of FIG. 11A with the released chemical reactant now reacting with the buttress material to color the buttress material to provide the surgeon with the visual indication.

Referring now to FIG. 11B, when the chemical substance 214 contacts the substrate 202, the substrate 202 will react with the chemical substance 214 to provide the visual indication that the optimal compression has been reached. The chemical reaction between the substrate 202 and the chemical substance 214 will change an optical property of the substrate 202 as shown in FIG. 11B, and in this manner, the surgeon will visually see a change in color at the desired site at the predetermined compression. Once being provided with the diagnostic indication and the surgeon will then know to apply the surgical element into the tissue T upon seeing the indication.

Figure 11C:
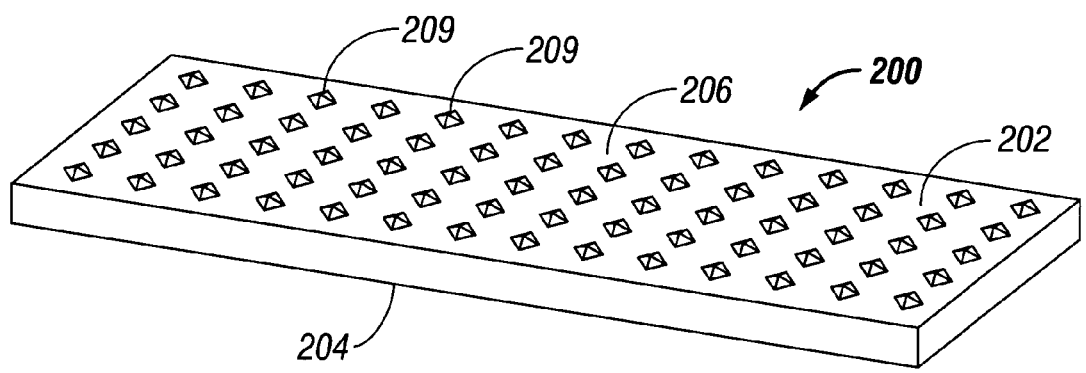
FIG. 11C is a perspective view of an embodiment of the substrate having a number of crystals to provide the surgeon with the visual indication.
Figure 11D:
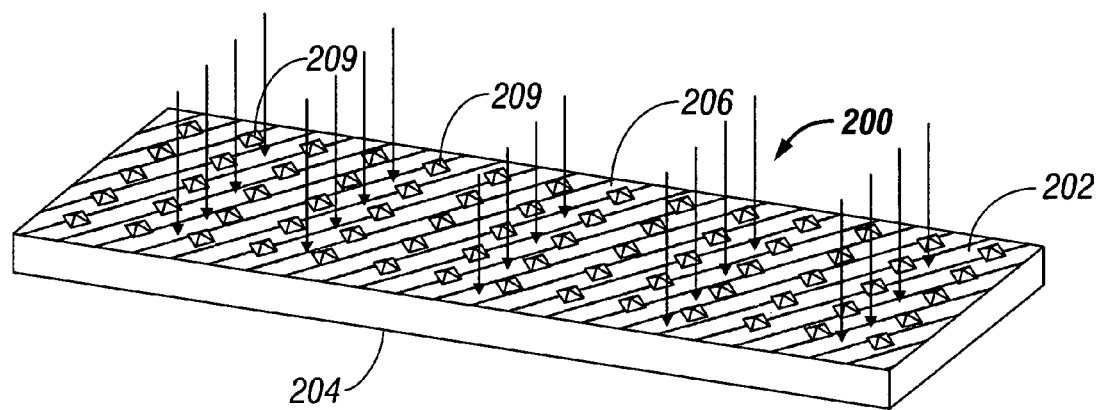
FIG. 11D is a perspective view of an embodiment of the substrate having a number of crystals subjected to the optimal compression and providing the visual indication.

In yet another embodiment of the present disclosure, the substrate 202 shown in FIG. 11C may be formed with a plurality of liquid or solid crystals 209. The crystals 209 are made with the substrate 202 and can be cast in place when the substrate 202 is manufactured. In one embodiment, the crystals 209 are cast into a polymeric material and the polymeric substrate 202 is extruded from a die. The crystals 209 have a predetermined initial state and a second state when compressed with the optimal amount of compression. Once the predetermined compression is reached in the procedure and applied to the substrate 202 as shown in FIG. 11D, the crystals 209 can break. In this manner, an optical property of at least one of the crystals 209 and the substrate 202 in response to the compression is changed to provide the indication. This indication permits the surgeon to instantly visually appreciate that the optimal compression has been reached.

It should be appreciated that with the substrate 202 fixed to the tissue, this allows the surgeon to inspect the tissue later or post firing or long after the firing of the instrument such as in post operative care. The surgeon may inspect the tissue adjacent the substrate 202 to ensure healing of the tissue, and that the proper amount of compression was applied to ensure a positive surgical outcome.

Figure 11E:
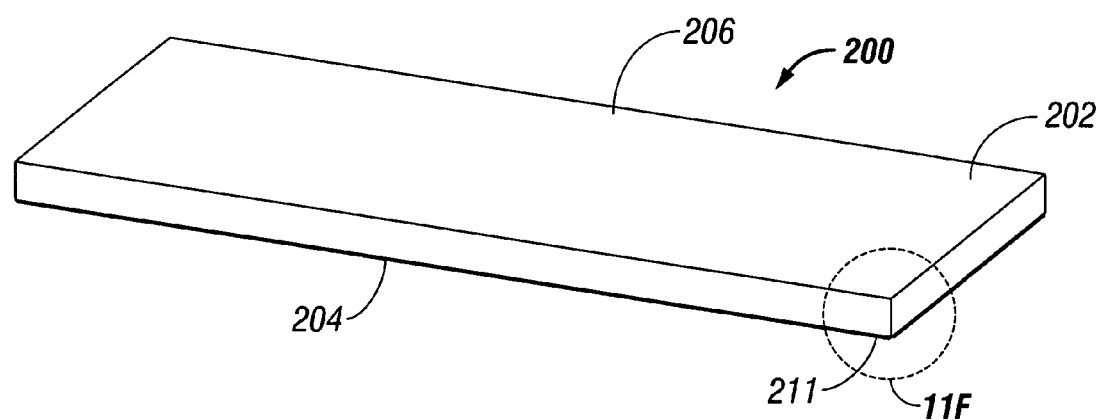
FIG. 11E is a perspective view of an embodiment of the substrate having a number of microspheres to provide the surgeon with the visual indication.
Figure 11F:
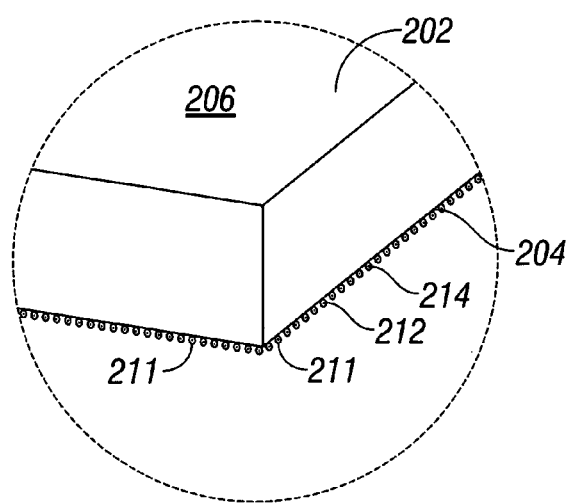
FIG. 11F is an enlarged view of detail of the embodiment of the substrate with the microspheres of FIG. 11E.

It should be appreciated that the sacs 208 may be formed with various sizes. In still another embodiment of the present disclosure as shown in FIG. 11E, the substrate 202 may be formed with a plurality of microspheres 211. The microspheres 211 are manufactured with the substrate 202 to include the dye 214 or other material as discussed above. In one embodiment, the microspheres 211 have a size that is of an order smaller relative to the sacs 208 of the previous embodiment. FIG. 11F shows an enlarged view of the substrate 202 along reference circle 11F of FIG. 11E. Once the predetermined compression is reached in the procedure and applied to the substrate 202 having the microspheres 211 on the distal surface 204, the microspheres 211 can rupture to release their contents and provide an indication in response to the optimal compression. This indication permits the surgeon to instantly visually appreciate that the optimal compression has been reached.

The microspheres 211 could be prepared from polymers including lactones, polyalkylene oxides, polyorthoesters, polyphosphazenes, vinyl polymers including polymethylmethacrylate, acrylic acid, methacrylic acid, styrene sulfonic acid, polyvinyl pyrrolidones, hydroxyethyl methacrylates, sulfopropyl acrylates, vinyl lipids and phospholipids, and vinyl copolymers, proteins (collagen, albumin, casein, gelatin, lactoferrin, synthetic/recombinant, etc.), polysaccharides (hyaluronic acid, carboxy methyl cellulose, heparin sulfate, dextran, chitosan, alginates, methyl cellulose, functionalized derivatives (amino, carboxy, hydroxy, sulfonated, fluorinated), etc.), polyesters, polyamines, polyanhydrides, polyhydroxy alkoanates, polyether esters, polymer drugs, or any combinations thereof.

Figure 11G:
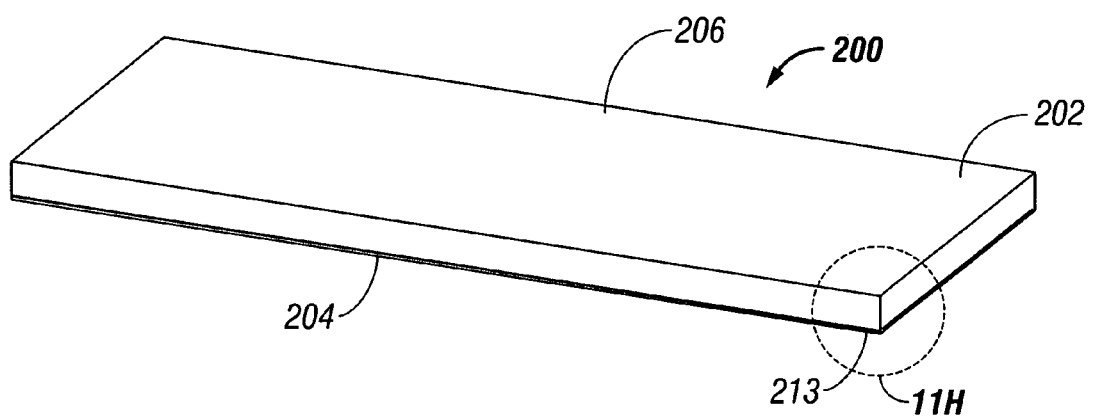
FIG. 11G is a perspective view of an embodiment of the substrate having a number of nano-spheres to provide the surgeon with the visual indication.
Figure 11H:
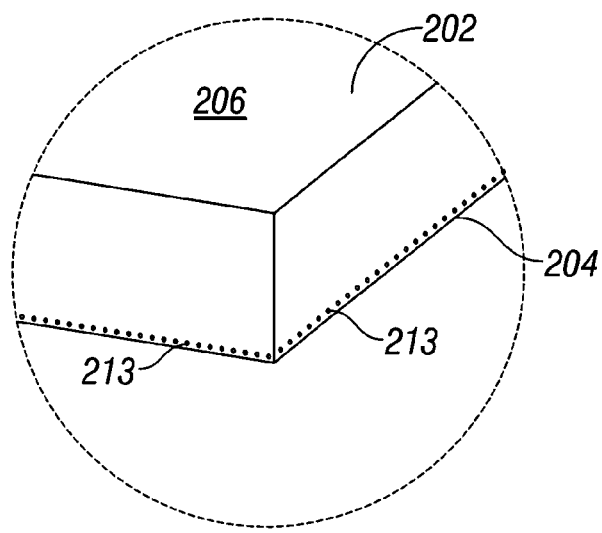
FIG. 11H is an enlarged view of detail of the embodiment of the substrate with the nano-spheres of FIG. 11G.

In still a further embodiment of the present disclosure shown as FIG. 11G, the substrate may be formed with a plurality of nano-spheres 213 which can be of an order of a tenth to $1000^{th}$ smaller than the sacs 208. The nano-spheres 213 are manufactured with the substrate 202 to include a material in a lumen (not shown) formed in each of the nano-spheres 213. In one embodiment, the nano-spheres 213 have a minuscule size relative to the sacs 208 of the previous embodiment. Once the predetermined compression is reached in the procedure and applied to the substrate 202 having the nano-spheres 213 shown in FIG. 11H, the nano-spheres 213 can rupture to release their contents and provide an indication in response to the optimal compression. This indication permits the surgeon to instantly visually appreciate that the optimal compression has been reached. In another embodiment, some of the nano-spheres 213 can rupture at different stress gradients to provide a number of different indications depending on the specific desired compression in the procedure.

Figure 12:
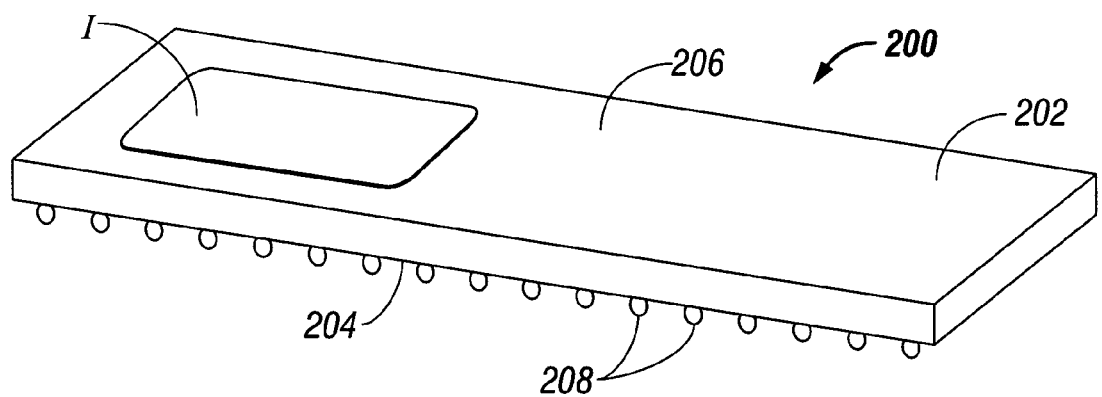
FIGS. 12 and 13 are perspective views of the buttress material for a specific tissue type.

In yet another embodiment of the present disclosure shown as FIG. 12, the substrate 202 may have a marking or identification on the proximal surface 206 to indicate a tissue type such as gastrointestinal tissue, cardiac tissue, pulmonary tissue, or muscle so the sacs 208 collectively will all yield when a certain amount of compressive force is placed on the substrate 202 that is relevant to that tissue type, and the surgeon can readily interchange between several different types of buttress materials 200 during the course of a single procedure. The contents of the sacs 208 may leak from the substrate 202 and on to the tissue T once the predetermined compressive force is achieved. In this manner, the surgeon will visually the indication at the desired site, and the surgeon will then know to apply the surgical element upon seeing the indication.

In yet a further embodiment of the present disclosure, the substrate 202 may have a marking or identification I on the proximal surface 206 to indicate a specific tissue condition for the tissue type. For example, for gastrointestinal tissue there may are several different substrates 202 with each having sacs 208 that will yield differently when a predetermined amount of compression is applied for different diseased or tissue types such as diabetic tissue. In one embodiment, the sacs 208 may yield at a first compressive force suitable for diabetic gastrointestinal tissue. The proximal surface 206 may provide such an indication I.

Figure 13:
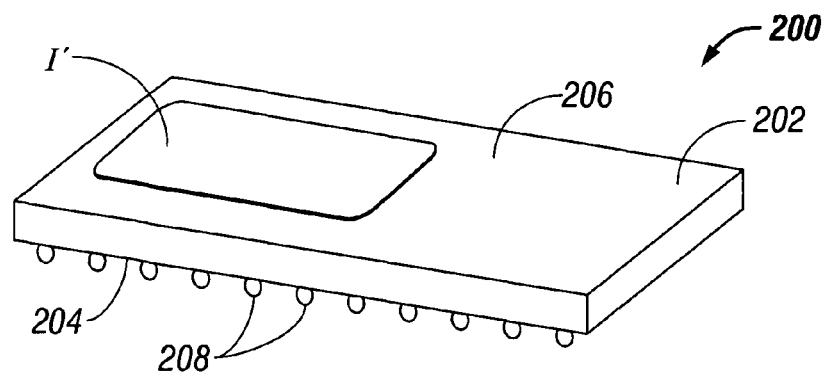

The sacs 208 in another embodiment may yield at a second compressive force that is different than the first compressive force and be suitable for ischemic gastrointestinal tissue. The proximal surface 206 will provide another indication I' such as "ischemic gastrointestinal tissue" as shown in FIG. 13. The sacs 208 in a further embodiment may yield and leak the dye 214 at a third compressive force that is different than the first and second compressive force and be suitable for gastrointestinal tissue where the patient has undergone extensive usage of a medicinal compound and be marked accordingly. In one example, where the medicinal compound is a steroid, the proximal surface 206 of the substrate 202 will provide such another indication I' such as "steroid use-gastrointestinal tissue" as shown in FIG. 13. Various configurations are possible and within the scope of the present disclosure.

The sacs 208 in other embodiments may yield at compressive forces suitable for various disease types, such as ischemic tissue, diabetic tissue, tissue exposed to specific prescribed medicine(s), soft tissue, thick tissue, or specific diseased tissue for all tissue types including but not limited to gastrointestinal tissue, pulmonary tissue, cardiac tissue, abdominal tissue, colonic tissue or any other known animal or human tissue.

It should be appreciated that the sacs 208 of the substrate 202 will not simply become leaky upon being compressed, but instead burst open to instantly provide the visual indication to the surgeon that the optimal compression from the instrument is reached. The sacs 208 may have a quantity of matter in the inner lumen 212 to assist with the bursting so as to come open or rupture suddenly when the optimal compressive load is applied to the substrate 202, especially from an internal pressure of the sac 208.

Figure 14:
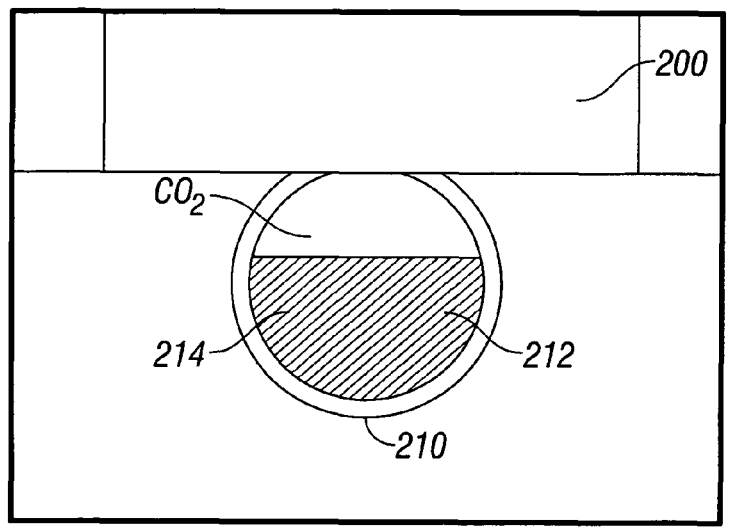
FIG. 14 shows an enlarged area of detail of a sac having a dye and a specific gaseous substance in the sac.

Referring to FIG. 14, the gas in the inner lumen 212 of the sac 208 that will burst may be air, oxygen, nitrogen, an inert gas, carbon dioxide or a specific predetermined other gaseous substance. The gas will further assist with bursting the lateral walls of the sac 208 when the certain amount of compressive force is placed on the buttress material 200 that is complementary to that tissue type.

It should be further appreciated that the sacs 208 further will burst open widely in order for the material being disposed in the sacs 208 to leak from the sacs 208 so as to become visible in a readily manner. The contents of the sacs 208 have little resistance to flow and a low viscosity. The contents leak from the sacs 208 and from the substrate 202 and on to the tissue once the predetermined compressive force is achieved in a readily manner. In this manner, the surgeon will immediately after the bursting visually appreciate a change in color at the desired site (or confined in the substrate 202) and the surgeon will then know to apply the surgical element upon seeing the indication.

Figure 15:
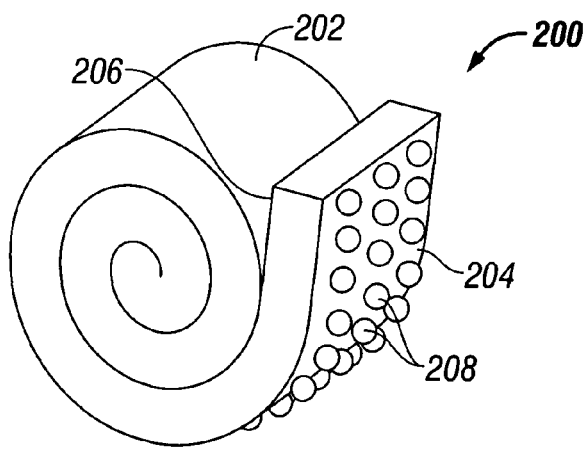
FIG. 15 shows a perspective view of a rolled buttress material for a specific tissue type.

The substrate 202 may be bendable without the sacs 208 bursting so as to be wrapped around the desired tissue site. In one embodiment, the substrate 202 may be arranged independent of the apparatus for applying a surgical element. The substrate 202 may be disposed in a suitable dispenser in a roll or laterally in a sealed box ready for surgical usage as shown in FIG. 15. The substrate 202 may be applied to a first side of the tissue, and then the jaws 22, 24 of the surgical instrument may be fashioned around the tissue and the substrate 202, and then compressed.

In another embodiment, two sheets of substrate 202 may be applied to a first side of the tissue, and then another opposite second side of the tissue. The jaws of the surgical instrument may be fashioned around the tissue and two sheets of the substrate 202 for compression. In still another embodiment, alternatively the substrate 202 may be arranged directly fixed on or through a slot in the jaws 22, 24 of a surgical instrument and connected to a suitable rolled dispenser adjacent to the instrument. Thereafter, the jaws 22, 24 may be compressed around the tissue and the substrate 202 to determine the optimal amount of compression. Thereafter, a portion of the substrate 202 formed in a roll may have a perforation (not shown). The used portion of the roll of the substrate 202 may be removed after the surgical element is introduced into tissue simply by tearing at the perforation.

It should be appreciated that the visualization of the color change may occur under natural lighting, or be observed under fluorescent lighting conditions. In one embodiment, the dye 214 may be visualized under a fluorescent light or at a predetermined wavelength such as 488 nm. In one embodiment, the surgeon can wear lenses or goggles to facilitate viewing the dye 214 and to assist with locating a proper staple line in order to introduce the surgical staples. Various configurations are possible and are within the present disclosure.

The substrate 202 may be applied dry to the tissue site, or with a suitable gel or lubricating agent. In one embodiment, the surgeon may apply lubrication such as VASOLINE™, or KY JELLY™, or another suitable gel such as maltodextran that permits the substrate 202 to be tacked down and remain on the tissue during compression.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments.

What is claimed is:

1. A surgical indicator to indicate proper formation of a surgical element comprising:
   a surgical buttress having a substrate made from a biocompatible material that is configured to be fixed to tissue by the surgical element, the substrate having a modulating property, wherein the substrate modulates from a first condition when no stress is applied to a second condition when a stress is applied; and
   wherein the modulating property is configured to provide an indication when compressed to a predetermined compression stress level, wherein the predetermined compression stress level indicates an optimal tissue compression for a tissue type, the indication being a tissue state that is optimal for the formation of the surgical element for the tissue type.

2. The indicator of claim 1, wherein the modulating property is a compartment having a dye, the compartment being made with a tensile strength that is configured to rupture at the predetermined compression stress level to release the dye to provide the indication.

3. The indicator of claim 1, wherein the indication is visual.

4. The indicator of claim 2, wherein the compartment bursts and the indication is audible.

5. The indicator of claim 1, wherein the substrate is a pressure sensitive film having a color when no stress is applied to the film, and wherein the pressure sensitive film is configured to indicate when compressed to the predetermined compression stress level to indicate the optimal tissue compression of the tissue type by changing color.

6. The indicator of claim 1, wherein the substrate is modulated from the first condition to the second condition by a surgical element in the form of a staple.

7. The indicator of claim 1, wherein the substrate is modulate from the first condition to the second condition by a surgical element in the form of a suture.

8. The indicator of claim 2, wherein the dye is non-toxic, and colors the tissue to another color.

9. The indicator of claim 2, wherein the substrate has the compartment that bursts to release the dye upon being compressed to the predetermined compression stress level, and wherein the dye is contained in the substrate and is not released on the tissue.

10. The indicator of claim 2, wherein the member has the compartment forming a lumen with a gas in the lumen, the lumen bursting open to release the dye and the gas in the inner lumen upon being compressed to the predetermined compression stress level.

11. An apparatus for determining an optimal amount of tissue compression prior to insertion of a surgical element into a tissue, comprising:
    a surgical buttress having a substrate being made from a predetermined biocompatible material and being configured to be fixed to tissue, wherein the predetermined biocompatible material has an initial color when no stress is applied to the substrate, and wherein the predetermined biocompatible material has a second color when a predetermined compression stress is applied to the substrate, the second color indicating a proper time to fire a surgical element into the tissue and the substrate to fix the substrate to the tissue.

12. The apparatus of claim 11, wherein the predetermined biocompatible material is a pressure sensitive film.

13. The apparatus of claim 11, wherein the predetermined biocompatible material is a pressure sensitive film, and wherein the pressure sensitive film changes color to indicate an area for a staple formation.

14. A surgical buttress material for use on a surgical stapler, the surgical stapler including an anvil and a lower jaw, the surgical buttress material comprising:
    a substrate made from a biocompatible material and configured to be fixed to tissue by a fastening element that is fired by the surgical stapler, the substrate including a surgical indicator having a modulating property, wherein the surgical indicator modulates from a first condition when no stress is applied to the substrate to a second condition when a stress is applied to the substrate; and
    wherein the modulating property is configured to provide an indication when the substrate is compressed to a predetermined compression stress level by the anvil and the lower jaw of the surgical stapler, wherein the predetermined compression stress level indicates an optimal tissue compression for a tissue type, the indication being a tissue state that is optimal for the formation of the surgical element for the tissue type.

15. The surgical buttress material of claim 14, wherein the modulating property is a compartment having a dye, the compartment being made with a tensile strength that is configured to rupture at the predetermined compression stress level to release the dye to provide the indication.

16. The surgical buttress material of claim 14, wherein the indication is visual.

17. The surgical buttress material of claim 14, wherein the substrate is a pressure sensitive film having a color when no stress is applied to the film, and wherein the pressure sensitive film is configured to indicate when compressed to the predetermined compression stress level to indicate the optimal tissue compression of the tissue type by changing color.

18. The surgical buttress material of claim 14, wherein the substrate is modulated from the first condition to the second condition by a fastening element in the form of a staple.

19. The surgical buttress material of claim 15, wherein the substrate has the compartment that bursts to release the dye upon being compressed to the predetermined compression stress level, and wherein the dye is contained in the substrate and is not released on the tissue.

\* \* \* \* \*